United States Patent [19]
Calenoff

[11] Patent Number: 5,567,594
[45] Date of Patent: Oct. 22, 1996

[54] METHODS AND COMPOSITIONS FOR THE DETECTION AND TREATMENT OF DISEASES ASSOCIATED WITH ANTIGENS OF MICROORGANISMS

[75] Inventor: Emanuel Calenoff, Chicago, Ill.

[73] Assignee: Enteron, L.P., Oak Brook, Ill.

[21] Appl. No.: 170,017

[22] Filed: Dec. 20, 1993

Related U.S. Application Data

[63] Continuation-in-part of Ser. No. 693,232, Apr. 26, 1991, abandoned.

[51] Int. Cl.$^6$ .................. G01N 33/53; G01N 33/554; G01N 33/569
[52] U.S. Cl. ............... 435/7.32; 435/7.33; 435/822; 435/883; 435/975; 436/513; 436/518
[58] Field of Search ................... 435/7.1, 7.2, 7.32, 435/7.33, 259, 883, 961, 962, 822, 41, 69.3, 975; 436/513, 518, 175, 825; 530/416

[56] References Cited

U.S. PATENT DOCUMENTS

| | | | |
|---|---|---|---|
| 3,983,008 | 9/1976 | Shinozaki et al. | 195/104 |
| 4,341,761 | 7/1982 | Ganfield et al. | 424/85 |
| 4,399,121 | 8/1983 | Albarella et al. | 260/112.5 R |
| 4,427,783 | 1/1984 | Newman et al. | 436/542 |
| 4,444,887 | 4/1984 | Hoffmann | 435/240 |
| 4,466,917 | 8/1984 | Nussenzweig et al. | 360/112 R |
| 4,472,500 | 9/1984 | Milstein et al. | 435/68 |
| 4,491,632 | 1/1985 | Wands et al. | 435/240 |
| 4,493,890 | 1/1985 | Morris | 435/7 |
| 4,539,292 | 9/1985 | Reid et al. | 435/7 |
| 4,849,337 | 7/1989 | Calenoff et al. | 435/7 |
| 4,870,053 | 9/1989 | Zalisz et al. | 514/8 |
| 5,262,156 | 11/1993 | Alemohammad | 424/92 |

FOREIGN PATENT DOCUMENTS

| | | |
|---|---|---|
| 0206324A2 | 4/1984 | European Pat. Off. . |
| 0296685A1 | 12/1988 | European Pat. Off. . |
| 0329570A2 | 6/1989 | European Pat. Off. . |
| WO90/03575 | 5/1990 | European Pat. Off. . |
| 0451800A1 | 10/1991 | European Pat. Off. . |
| 1603305 | 10/1990 | U.S.S.R. . |
| WO92/19970 | 11/1992 | WIPO . |
| WO94/23728 | 10/1994 | WIPO . |

OTHER PUBLICATIONS

O'Toole, P.W., et al, J. Bacteriol 1991, 173:505–513, Molecular cloning and expression of Campylobacter pylori species–specific protein antigen from the gastric pathogen Helicobacter pylori.

Karita, M. et al., Am J. Gastroenterol, 1991, 86:1569–1603, New small animal model for human gastric Helicobacter pylori infection: success in both nude and euthymic mice.

Varga, L. et al., Orv Hetil, Feb. 9, 1992, 133(6):359–361, Helicobacter pylori allergy.

Czinn et al., Gastroenterology 100, No. 5, pt. 2, A571, 1991, Serum and Mucosal Immune response following Oral Immunization with Helicobacter Pylori.

Czinn et al., Gastroenterology, 102, No. 4, pt. 2, A611, 1992, Oral Immunization Protects Germ–free Mice against infection from Helicobacter Felis.

Newell, DG Scand, J. Gastroenterol Suppl (Norway), 1991, 187, pp. 31–38, Virulence factors of Helicobacter pylori.

Hai, UE et al., J. Clin Invest (United States) Mar 1991, 87 (3) pp. 894–900, Soluble surface proteins from Helicobacter pylori activate monocytes/macrophages by lipoploysaccharde–independent mechanism.

Bhaduri, S. et al., Appl Environ Microbiol (United States), Oct. 1983, 46(4) pp. 1941–1943, Simple and rapid method for disruption of bacteria for protein studies.

Moser, EH et al., J. Steroid Biochem, Jun. 1989, 32(6) pp. 759–767, Purification and characterization of a heat and acid stable progestin binding protein of rat lung.

Slomiany, BL et al., Biochem Biophys Res Commun, Mar. 16, 1992, 183(2) pp. 506–513, Glycosulfatase activity of Helicobacter pylori toward gastric mucin.

Leung et al, J. Clin Invest, 92(3):1374–1380, Sep. 1993.

Shen et al, Clin Exp. Allergy 19(2):191–196, 1982.

Calenoff et al., (1993). Bacterial Allergy in Nasal Polyposis. *Arch Otolaryngol. Head Neck Surg.*, 119:830–836.

Calenoff et al., (1983). Bacteria–Specific IgE in Patients with Nasal Polyposis. *Arch Otolaryngol.*, 109;372–375.

Shahamat et al., (1989). Production and Characterization of Monoclonal Antibodies to *Campylobacter pylori*. Abstract of the Annual Meeting–1989. V–24, p. 490.

Ceska et al. "Radioimmunosorbent Assay of Allergens", *J. Allergy and Clin. Immunol.* 49:1, 1972.

Dreesman et al. "Anti–Idiotypic Antibodies: Implications of Internal Image–Based Vaccines for Infectious Diseases", *J. Infect. Diseases*, vol. 151, No. 5, pp. 761–765, May 1985.

Eaton et al. "Campylobacter Pyroli Virulence Factors in Gnotobiotic Piglets ", *Infection & Immunity*, vol. 57, No. 4, pp. 1119–1125, Apr. 1989.

Grzych "An Anti–Idiotype Vaccine Against Experimental Schistosomiasis", *Letters to Nature*, vol. 316, pp. 74–76, Jul. 1985.

Hupertz et al. "Demonstration of a Cytotoxin from Campylobacter Pyroli" *Eur. J. Clin. Microbiol Infect. Dis.*, vol. 7, pp. 576–578, 1988.

(List continued on next page.)

Primary Examiner—Marian C. Knode
Assistant Examiner—Patricia A. Duffy
Attorney, Agent, or Firm—Brinks Hofer Gilson & Lione

[57] ABSTRACT

A library of isolated and purified antigens specific for a microorganism is a set of individual molecules. The library forms antigen-antibody complexes useful in the context of diagnosing and treating conditions associated with a specific microorganism such as *H. pylori*-induced gastro-duodenal disease. For the antigen-antibody complexes in question the antibody is an immunoglobulin, which is IgE if the antigens are allergens. Complexes with IgA, IgG and IgM are also useful. By this multivariate approach, a specific condition is diagnosed with high sensitivity and specificity by determining whether complexes form between a specific antigen library and a biological sample which contains immunoglobulins from an individual. Such libraries also are useful for immunotherapy.

15 Claims, 5 Drawing Sheets

OTHER PUBLICATIONS

Lambert et al. "Diffuse Varioliform Gastritis ", *Digestion*, vol. 17, pp. 159–167, 1978.

McNamara et al. "Monoclonal Idiotype Vaccine against Streptococcus Pneumoniae Infection ", *Science*, vol. 226, pp. 1325–1326, Dec. 1984.

Warren "Unidentified Curved Bacilli on Gastric Epithelium in Active Chronic Gastritis", *Lancet*, vol. 1, pp. 1273, Jun. 1983.

Marshall *Lancet*, vol. 1, pp. 1273–1275, Jun. 1983 (Attached to Warren reference).

Nalebuff et al. "The Study of IgE in the Diagnosis of Allergic Disorders in an Otolaryngology Practice" *Otolaryngol Head & Neck Surg.*, vol. 87, pp. 351–358, May–Jun. 1979.

Nalebuff et al. "Determination of Initial Immunotherapy Dose for Ragweed Hypersensitivity with the Modified Rast Test", *Otolaryngol Head & Neck Surg.*, vol. 89, pp. 271–274, Mar.–Apr. 1981.

Nisonoff et al. "Implications of the Presence of an Internal Image of the Antigen in Anti–Idiotypic . . . " *Clin. Immunol. Immunopath.*, vol. 21, pp. 397–406, 1981.

Peterson "Helicobacter Pyroli and Peptic Ulcer Disease", *New England J. Med.*, vol. 324, No. 15, pp. 1043–1048, Apr. 1991.

Slomiany et al. "Lipolytic Activity of Campylobacter Pyroli: Effect of Colloidal Bismuth Subcitrate . . . " *Am. J. Gastroenterology*, vol. 84, No. 10, pp. 1273–1277, 1989.

Smibert "The Genus of Campylobacter", *Ann. Rev. Microbiol.*, vol. 32, pp. 673–709, 1978.

Uytdehaag et al. "Induction of Neutralizing Antibody in Mice Against Poliovirus Type II with Monoclonal . . . " *J. Immunol.*, vol. 134, No. 2, pp. 1225–1229, Feb. 1985.

Aceti et al. "Basiophil–Bound and Serum Immunoglobulin E Directed Against Helicobacter Pyroli In . . . " *Gastroenterology, vol. 101, No. 1, pp. 131–137, Jul. 1991*.

Gleich et al. "Measurement of IGG Blocking Antibodies by Interference in the Radioallergosorbent . . . " *J. Immunol.*, vol. 126, No. 2, pp. 575–579, Feb. 1981.

Weir Handbook of Experimental Immunology, *Blackwell Scientific Publications*, pp. 2.1–2.17, 1978.

Scott "Monoclonal Antibodies–Approaching Adolescence in Diagnostic Immunoassays", *Trends in Biotechnology*, vol. 3, No. 7, pp. 170–175, 1985.

Andre et al, Annuals of Allergy, 51:325–328 (Aug. 1983).

Evans et al, Gastroenterology, 96(4):1004–1008 (1989).

Hirschl et al, J. Clin Pathol., 43:511–513 (Jun. 1990).

Deutscher, Methods in Enzymology vol. 182 Guide to Protein Purification Academic Press Inc © 1990 pp. 253–264 and 285–300.

Harlow et al, Antibodies a Laboratory Manual, Cold Spring Harbor Laboratory © 1988 pp. 613–625.

Catty, Antibodies vol. 1 A Practical Approach, IRL Press, Oxford © 1988 pp. 74–75.

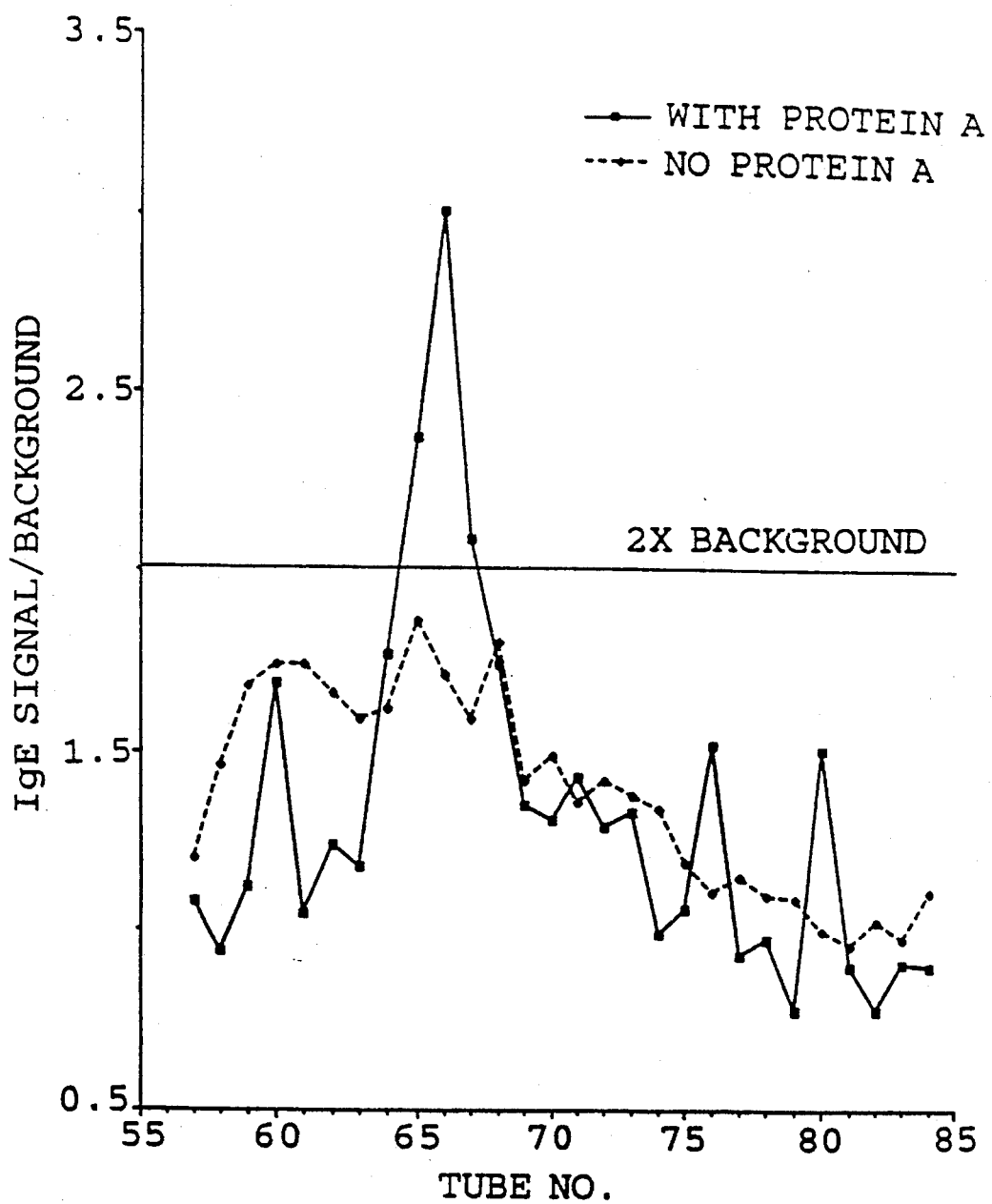

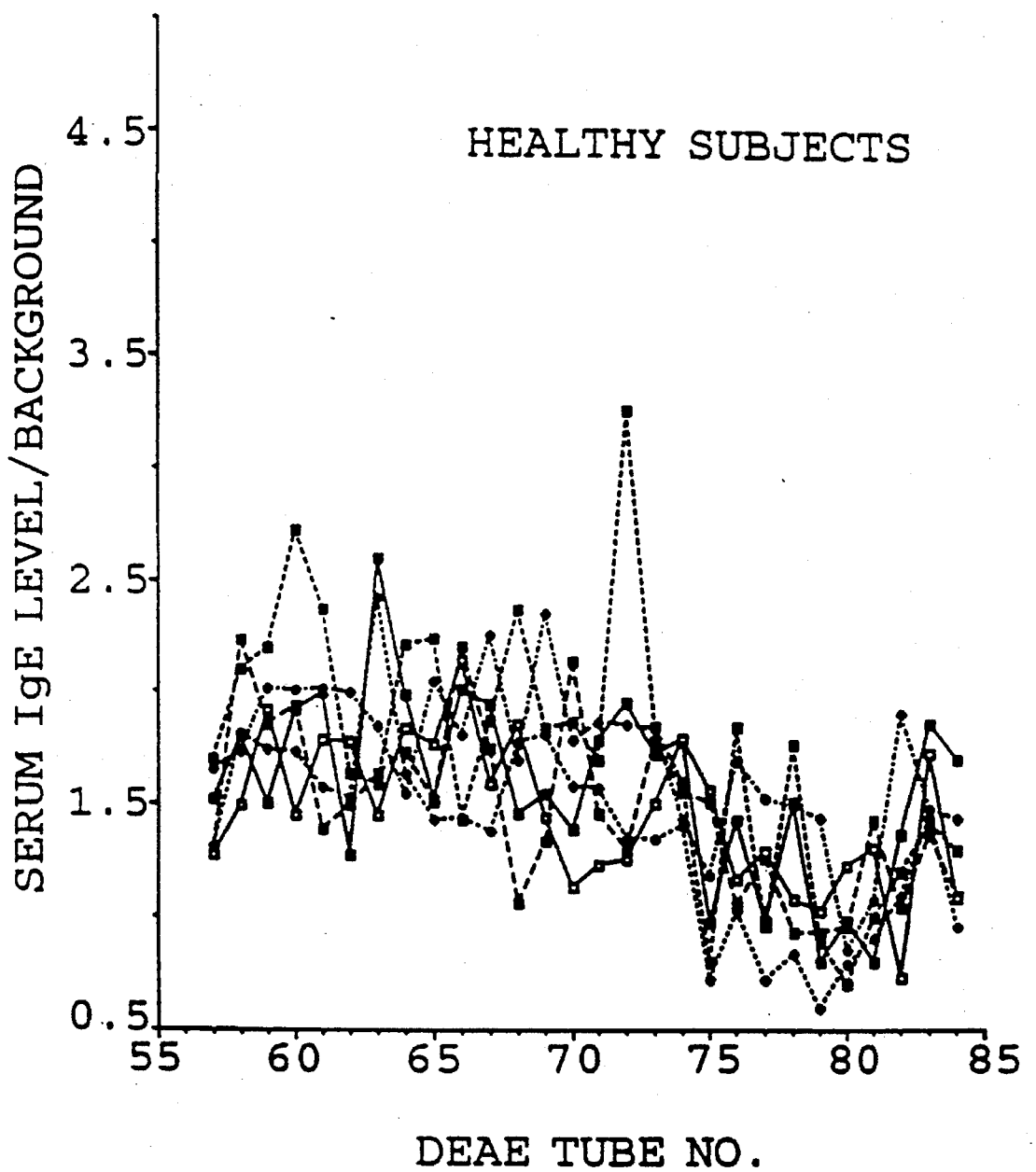

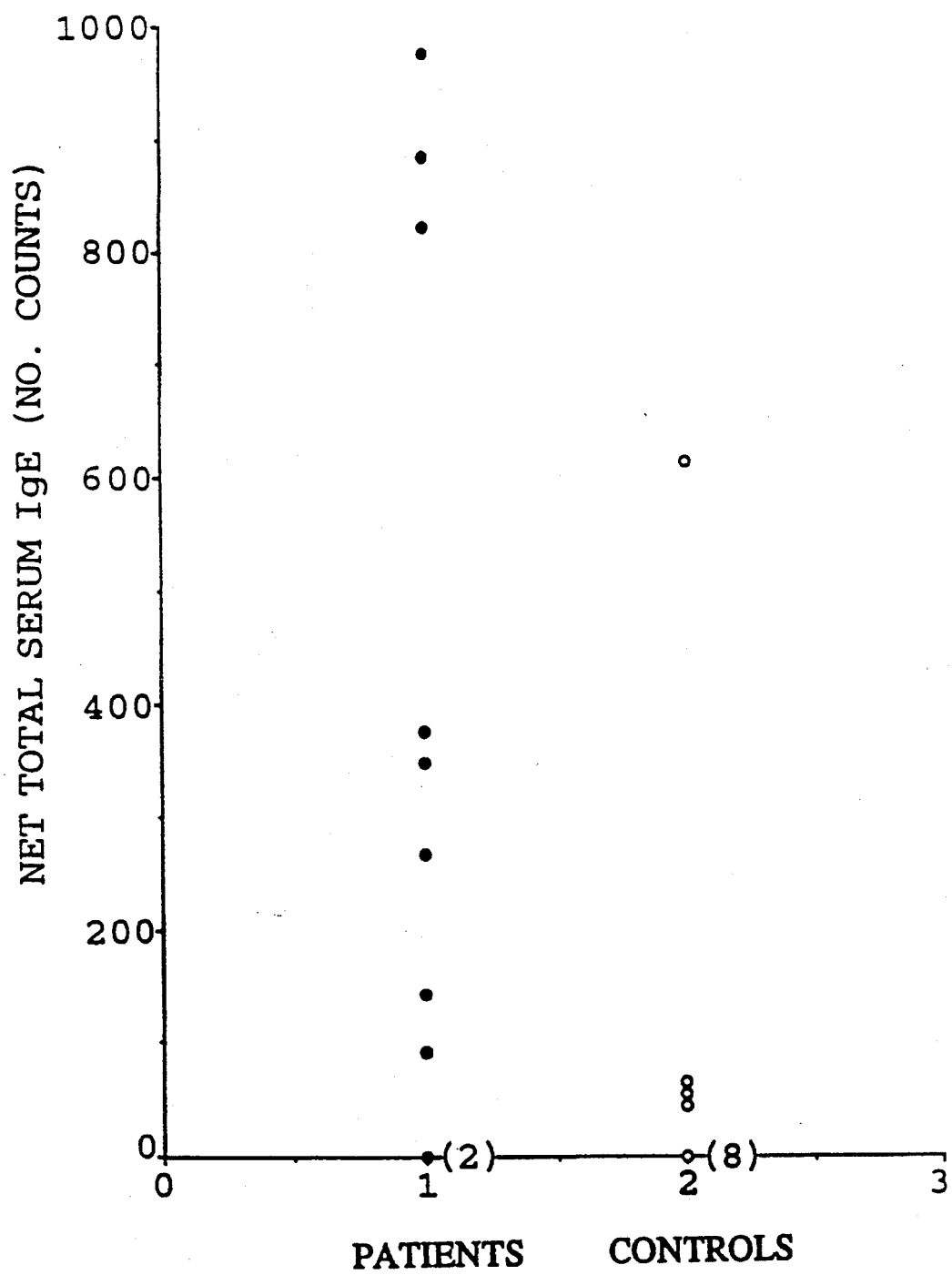

METHODS AND COMPOSITIONS FOR THE DETECTION AND TREATMENT OF DISEASES ASSOCIATED WITH ANTIGENS OF MICROORGANISMS

CROSS REFERENCE TO RELATED APPLICATION

This application is a continuation-in-part and claims priority under 35 U.S.C. §120 from U.S. patent application, Ser. No. 07/693,232, filed Apr. 26, 1991 which is now abandoned.

BACKGROUND OF THE INVENTION

The present invention relates to methods and compositions for the detection and treatment of a disease or condition associated with microbial antigens, more specifically to the isolation and purification of bacterial antigens, and to their use in diagnosis and treatment.

A number of idiopathic recurrent diseases are of unknown etiology. Some of these diseases are believed to be linked to infection by a microorganism, for example, a bacterium. However, the causal relationship between the microorganism and the disease is not established for many of these diseases or conditions. Even in diseases or conditions showing an association with an infectious agent, the etiology leading to the disease symptoms is generally unknown. For some diseases, such as chronic gastritis and peptic ulcer disease, and chronic inflammatory diseases of the nose and paranasal sinuses, a link is suspected between infection and allergy. The initiating event is suspected to be an infection, with allergy developing as a sequel. Subsequently, infection may exacerbate the microbial allergy which leads to both chronic hypersensitivity and chronic infection. Data in support of these theories is not capable of discriminating between them.

It has been suggested that bacterial allergy may play a significant role in chronic diseases of the aerodigestive tract. Examples of aerodigestive diseases potentially effected by bacterial hypersensitivity include asthma, nasal polyps, chronic gastritis and gastric ulcer disease. At present, no uniform view exists as to how the allergic process is mediated or, more precisely, how mast cell degranulation is induced. A bacteria-specific IgE-mediated response is postulated for some diseases in this category.

IgE-mediated reactions resulting in chronic inflammation rather than acute, short-lived reactions have been well described. The hallmark event described in these studies is mast cell degranulation. Mast cells release vasoactive mediators and late-phase reactants, such as chemotactic agents, recruit neutrophils, eosinophils, and monocytes. The influx of these cells is followed by lymphocytic infiltration. These events may become part of a chronic, repetitive process through the maintenance of a protracted mast cell degranulation.

Digestive diseases include the related disorders of chronic gastritis and peptic ulcer disease which appear to be associated with the microorganism Helicobacter pylori, but the nature of the association, and the mechanisms linking infection with subsequent symptoms are not known. Unraveling the etiology of these diseases is important because chronic gastritis and peptic ulcer disease are diseases of major significance. Five to ten percent of all individuals develop chronic gastritis and/or gastroduodenal ulcers in their lifetime. Ulcer disease is a common cause of morbidity. The annual prevalence of symptomatic peptic ulcer disease in the United States of America is approximately 18 per 1,000 adults (or about 4,500,000 people). Approximately 350,000 new cases of peptic ulcer disease are diagnosed each year.

Diagnosis of these diseases is usually performed by gastroduodenal endoscopy, an invasive and costly procedure. Treatment encompasses oral medication, dietary controls, and surgery. Rarely is treatment successful in effecting a "cure," rather these chronic conditions are characterized by cycles of improvement and relapse.

Since the report by Marshall (1983) that the bacteria *Helicobacter pylori* is physically associated with the lesions of chronic gastritis, a great deal of work has been done in an effort to elucidate a causal relationship between the organism and the chronic disease. Early speculations regarding localized pH changes induced by *H. pylori*, the release of toxins (Hupertz et al., 1988), and destructive enzymes (Slomiany et al., 1989) and the differences between different strains of the bacteria (Eaton et al., 1989) have not resulted in firm conclusions that are accepted in the art concerning the etiology of the disease (Peterson, 1991). Moreover, the search for a reasonable explanation of cause and effect has been further complicated by the recognition that a significant number of clinically well subjects also carry the presumptive infectious organism. Clearly, diagnostic tests directed solely at *H. pylori* would not have a suitable specificity. Therefore, for these diseases and others related to an infectious agent, new approaches are needed.

It is known that microbial proteins may be antigenic, and possibly allergenic. But there has been no systematic pursuit of a set of individual antigenic molecules that derive from a microorganism and that highlight interactions between the microorganism and a host to produce symptoms of a disease or condition.

Measurements of total immunoglobulin, even if a certain type, is a relatively crude assay because it measures a response to many antigens from many sources. Attempts to develop serological tests consisting of detecting antibodies in serum to crude extracts of bacteria have had unacceptably high false positive and false negative rates (Evans, 1989). Use of purified antigens showed some improvement. At most, assays for one antigen or allergen, or for a crude composite of antigens or allergens, are available for clinical diagnosis, but are unsatisfactory. Multivariate approaches to define a set of individual antigens specific for a microorganism, and to determine an immunological response with increased sensitivity and specificity have not been suggested.

It also is recognized that there are immunological responses of a host to the presence of a microorganism. Yet immunological profiles have not been identified heretofore that are specific for complexes between a set of individual microbial antigens and host serum antibodies which identify an organism associated with a disease or condition.

SUMMARY OF THE INVENTION

Pursuant to the present invention a microorganism associated with a disease or condition is not directly detected. Instead, an immunological response profile of the infected host is detected which reflects reaction of the host to a library of individual antigens specific for the presence of the microorganism.

The methodology of the present invention elevates the search for disease related antigens, particularly, antigens that stimulate an allergic response, from a "needle in a haystack" approach to one based on a sophisticated plan leading to detection of specific host invaders that produce clinical symptoms. Multivariable diagnostic criteria based on identification and quantification of immunoglobulins binding to a library of specific antigens are used to detect specific diseases or conditions and to differentiate them from related diseases or conditions.

The diagnostic methods disclosed herein have great flexibility because they are based on a library of microbial antigens from which a test vector is selected depending on the specificity-sensitivity levels desired. Because specificity and sensitivity are correlated, altering one value generally affects the others. Choice of a test vector follows assay optimization techniques wherein antigen groupings are mixed and matched to obtain the desired balance of sensitivity and specificity. Tests designed to increase sensitivity generally do so at the risk of lowering specificity. The present invention permits the modifying of these values for particular situations. Because there are large numbers of antigens in a library, there are many subsets that may be generated for a particular assay. Also, because changes in IgE, IgA, IgG and IgM directed to the set of chosen antigens are monitored, comprehensive rather than "one shot" information is provided for an individual being tested.

By means of the present invention, an immunological response is detected that occurs in a host and is correlated with clinical suspicion of a disease, such as chronic gastritis and peptic ulcer, to arrive at a diagnosis. Discrimination between diseases with similar symptoms is facilitated by testing not for the response to only one antigen, but rather by testing for the response to a library of antigens determinative of the presence of a particular bacterium in a particular disease state or condition for example, *H. pylori* and gastric cancer, *Staphylococcus aureus* and nasal polyposis or hyperplastic sinusitis. This novel concept is extendable to disorders related to bacterially stimulated allergic responses, wherein detection of immunoglobulins such as IgE directed to protein subfractions of a bacteria, opens the door to a complex, multivariable approach to diagnostic assays, and exposes the mechanisms producing disease symptoms.

The methods of the present invention include chemically dissecting a microorganism such as a bacterium, a virus or a mycoplasma, into purified protein (antigenic) subfractions, each terminal subfraction containing an individual molecule capable of eliciting an immunological response in a host. The identifying subfractions are produced by dissecting a microorganism so finely into its individual molecular components, that subfractions or a combination thereof which include the constituent molecules are produced that uniquely identify the microorganism. Generation of purified antigens also enhances binding of immunoglobulins to a specific antigen because specific antigen absorption sites or coupling sites on a test surface are not cluttered with contaminating, non-specific antigens.

A method for isolating and identifying individual microbial antigenic proteins includes the steps of treating the microorganism, preferably a bacterium, with increasing concentrations of sodium dodecyl sulfate (SDS) and precipitating proteins (polypeptides) within each SDS preparation with increasing concentrations of acetone. Polyacrylamide gel electrophoresis is used to further separate the polypeptides by molecular weight. By this process, an individual molecule is isolated and may subsequently be visualized by labelling bands on the gel, for example. A library (protein bank) of such proteins is generated from a particular species of microorganism, such as those enumerated in Table 1 below. An "individual molecule" is a single species as identified by molecular weight, isoelectric point, solubility and the like. The purification methods of the present invention produce in the terminal subfractions, that is, after the last acetone treatments, individual molecules.

In accordance with another embodiment of the present invention, preparing purified protein antigens, which may also be allergens, can be accomplished by (a) treating bacterium containing a protein allergen with acetone to remove lipid components; (b) disrupting the acetone-treated bacterium in a solution comprised of buffer, salt, metal chelator, protease inhibitor, and benzamidine; (c) separating a protein containing fraction from complex carbohydrates and nucleic acids; (d) collecting a composition comprised of proteins which are of molecular weight at least about 1,000; and (e) separating the proteins of the composition of (d) by ion-exchange chromatography. This embodiment, however, does not yield antigens as pure as those produced by the SDS acetone method described in a previous paragraph. Under standard assay conditions, the purer the microbial antigen, the larger are the number of specific antigen sites available for binding with antigen specific immunoglobulin. An advantage of the purified antigens from the SDS-acetone methods of the present invention is that they are detectable by one immunoglobulin isotype in the presence of other isotypes.

By use of the SDS-acetone method, a library of antigens is derived from fractionating a microorganism into individual molecules identified as bands of a uniform molecular weight, and determining that each individual molecule is capable of complexing with an immunoglobulin. From that initial library, subsets are selected for different purposes.

To facilitate collection of bacterial antigens in a quantity adequate for use in diagnosis and treatment, production of the antigens by recombinant genetic technology is preferred.

If the library is to be used for screening purposes in an assay in which the immunoglobulin response will be detected in the aggregate, a large enough library is selected to generate a detectable signal, for example on a paper disc. For this purpose, antigens derived from a particular microorganism that are not unique to that microorganism, may be included.

Because not all patients may react with the same subset of antigens within the basic library, enough antigens are included in the assay so that a detectable signal is generated from all patients having a particular condition. This means a positive test (signal detectable at a predetermined level) may differ in its antigenic composition for patients having the same condition.

The number of antigens required to detect a condition is a function of specificity and sensitivity levels desired, and the labelling method used. If, for example, it is more important not to include non-affected individuals as false positives, that is, a high specificity is desired, a relatively smaller subset of highly specific antigens from the library is selected.

However, the largest subset of antigens from a library generally will provide optimum sensitivity and specificity. Sensitivity is improved because enough pure antigens are provided to be detected by one isotype in the presence of other specifically-reactive antibodies of other isotypes. Assays based on a single antigen generally have poor sensitivity, although they may be highly specific because not all patients may be sensitive to a particular antigen, or the antigen is not expressed by all subspecies of a particular microorganism. The use of a family of antigens in the present invention solves the problem.

In some diseases or conditions, more than one microorganism may be implicated in causality of a disease by relatively crude analysis such as culturing organisms from a clinical sample. Not all of these microorganisms may prove to be specific for a disease or condition, as determined by methods of the present invention. Comparison of immunological profiles of individuals in response to antigen libraries prepared from the different microorganisms suspected of association with the condition, may reveal the microorganism primarily responsible for characteristic symptoms, and may differ from incidental agents. An organism that is incidental will not show an IgE response, or will not show as strong an IgE response, as an organism operating as an allergen provider responsible for the condition.

The immunological response of each protein library (protein bank) is tested for a specific immunoglobulin reactivity. A profile is then developed of antigens eliciting a response from persons having a particular disease or condition.

A profile is defined as an immunological response to a set of specific individual antigenic molecules isolated in subfractions prepared from a microorganism. The ability of the antigens to discriminate between persons with and without a condition is determined by the specificity of the immunological response to a library of antigens in a sample from a person with a disease or condition, as compared with a control sample. An adequate control is defined, depending on the condition to be identified. Adequate controls include individuals without the condition, without clinical symptoms of a disease, or with a disease or condition in which a differential diagnosis is desired. Controls are ideally matched or standardized for variables known to stimulate an immunological response. Immunological profiles are comprised of the types of immunoglobulin produced and the amount of each type produced. Immunoglobulins suitable for the practice of the invention include IgA, IgM, IgG and IgE.

IgE is preferred as the immunoglobulin used in the initial assay because positive values indicate the presence of an allergen, and because IgE responses are more characteristic of the conditions to be detected within the scope of the present invention.

An IgE response usually indicates chronic or protracted exposure to an antigen and requires a longer exposure to evolve, compared to the other immunoglobulins such as IgA, IgG or IgM which arise relatively quickly in the presence of an antigen.

After the IgE-mediated response is detected, however, monitoring the condition, particularly as to a response to treatment, is preferably accomplished by ascertaining IgA, IgG and/or IgM, levels in addition. A vector of responses for the immunoglobulin types reveals more than values for one immunoglobulin alone.

A profile specific for a microorganism is identified by binding of an immunoglobulin type to a library of antigenic subfractions of the microorganism associated with the disease.

An individual molecule or a combination thereof is detected by measuring the immunological response of the host in the presence of the subfraction containing the molecule, although in the host, the subfraction is generally part of an intact microorganism.

Microbial specific protein subfractions are identified by measurement of serum immunoglobulin levels, IgE, IgM, IgG and IgA, indicating that microbial specific immunoglobulin is quantifiable. IgE response is the preferred initial screening assay because reaction with this immunoglobulin type is more specific for an antigen library. An IgE response generally indicates chronic exposure to an antigen, and requires a longer exposure to develop. The other immunoglobulins arise more quickly and are more likely to reflect random or sporadic, rather than causal, exposure. After the IgE response is detected, reactions with IgA, IgG and IgM are useful in addition to monitor responses of individuals to treatment and/or disease progression.

TABLE 1

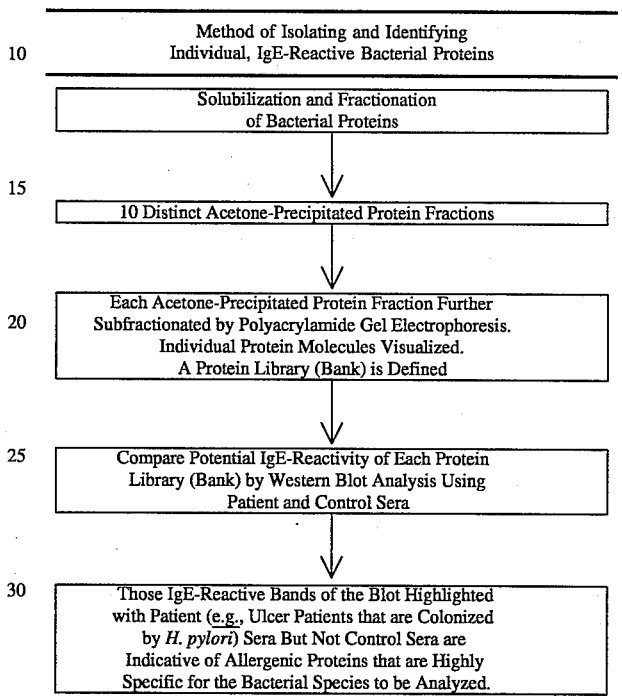

Method of Isolating and Identifying Individual, IgE-Reactive Bacterial Proteins

Solubilization and Fractionation of Bacterial Proteins

↓

10 Distinct Acetone-Precipitated Protein Fractions

↓

Each Acetone-Precipitated Protein Fraction Further Subfractionated by Polyacrylamide Gel Electrophoresis. Individual Protein Molecules Visualized. A Protein Library (Bank) is Defined

↓

Compare Potential IgE-Reactivity of Each Protein Library (Bank) by Western Blot Analysis Using Patient and Control Sera

↓

Those IgE-Reactive Bands of the Blot Highlighted with Patient (e.g., Ulcer Patients that are Colonized by H. pylori) Sera But Not Control Sera are Indicative of Allergenic Proteins that are Highly Specific for the Bacterial Species to be Analyzed.

Another aspect of the present invention is a method of determining whether an individual has a immunological response to a bacterial antigen, the method including (a) providing serum from an individual suspected of containing the immunoglobulin directed to the antigens of the agent; (b) providing a composition consisting essentially of a purified specific antigenic library; (c) reacting the serum of (a) with the composition of (b) under conditions which allow immunological binding between antibody and an antigen to which it is directed; and (d) detecting complexes formed, if any, between antibodies in the serum of (a) and each of the individual protein antigens in the composition of (b).

Accordingly, the present invention contemplates a method of measuring IgE which bind(s) immunologically to an allergenic protein(s). Serum suspected of containing the IgE is reacted with an extract of the microorganism coupled to a solid support, followed by washing and reacting with labelled anti-IgE, and detecting labeled anti-IgE bound to the solid support.

A suitable method of identifying allergic immunological responses is to couple one or more allergenic proteins (polypeptides) which include epitopes to a solid substrate. A biological sample, such as serum or tissue fluids, suspected of containing IgE specific for the allergens is reacted with the allergen-substrate complex. IgE that reacts immunologically with the allergen of the complex is detected by methods such as Western Blots and ELISA (enzyme-linked immunosorbent assay). Because anti-isotype antibodies are available, the immunoglobulin may be identified and quantified without separating isotypes. Enhanced sensitivity is a result of providing enough pure antigen so that even if more than one isotype of antigen specific immunoglobulin binds to the antigen, each is detectable separately.

The reason that the effect of each isotype is detectable against a background of the other isotypes, is that there is sufficient antigen available so that binding sites are available to accommodate specifically-reactive immunoglobulins of all isotypes. Competition for sites does not dilute binding of an isotype such that label detection of each isotype is obscured.

An example of an assay which is suitable for detecting IgE directly to crude antigen extracts is the Radioallergosorbent (RAST) test. In a modified RAST test, purified protein allergens are linked to a solid support.

If the proteins are not purified enough so that sufficient sites are available for binding of all isotypes to a degree that the binding is detectable, prior to reaction with the protein allergens, the serum to be tested is treated to remove IgA, IgM and/or IgG. This "scrubbing" step is suitable for the detection of the allergen-specific IgE. "Scrubbing" is not required for a RAST test if the purified antigens of the present invention from the SDS-acetone method are used in sufficient quantities.

Via an illustrative embodiment of the present invention which employed a modified PAST test, it was discovered for the first time that there was a high positive correlation between gastritis/ulcer disease and the presence of IgE directed to specific subfractions of protein allergens of H. pylori. These results were direct evidence, for the first time, that an adverse immune reaction to these bacteria is responsible for the pathological reaction in the host, in particular, as evidenced by the existence of a hypersensitivity reaction mediated by specific IgE components.

The identification of protein allergens of H. pylori associated with gastritis/ulcer disease allows for a relatively non-invasive detection of the disease. In addition, it also allows for treatment of the disease by immunotherapy, using purified protein allergens.

Investigation of bacterium-specific IgE fractions is not limited to diseases associated with H. pylori. in addition, immunoglobulins other than IgE (IgA, IgG, IgM) are suitable for the practice of aspects of this invention.

Another aspect of the invention is a composition consisting essentially of a purified antigenic subfraction prepared from a microorganism by the methods of the present invention. Specifically, the subfraction or combination thereof includes at least two bacterial antigens. More specifically, subfractions are derived from Helicobacter, Pseudomonas, Streptococcus and the like.

Another aspect of the invention is a set of protein antigens (library, protein bank) coupled to a solid substrate. The set includes antigens specific for H. pylori.

A "set" (library, vector, protein bank) of antigens is defined as polypeptides that invoke an immunological response and distinguish a biological sample from an individual with a condition, to a sample from an individual without the condition.

In an illustrative embodiment, comparison of serum from individuals affected with a condition or disease, to serum from control (unaffected) individual shows the power of such a procedure for isolating and identifying individual, IgE-reactive bacterial proteins. IgE-related molecular bands on a solid support that are highlighted and are present in serum from the affected, but not from control samples, are highly diagnostic for a disease or condition, for example, H. pylori and peptic ulcer in Table 1. The problem of false positives in well persons using a direct assay for H. Pylori is alleviated because only an H. pylori-stimulated response is scored as positive.

It was unexpected that antibodies produced to the subfractions containing isolated and purified bacterial antigens are capable of teasing out subtle differences in the antigenic components of even closely related species or differences in allergic responses of the host. It was also unexpected that a signal signifying antigen-antibody binding to one immunoglobulin isotype is detectable in the presence of others.

Moreover, even in situations where the presence of an infectious agent does not discriminate between the presence or absence of a disease, the severity of a disease may be determined by quantifying the immunoglobulin response to an antigenic profile of the agent.

The problem of false positives using currently known or available assays for H. Pylori in well persons is alleviated because only an H. pylori-specific response is scored as positive.

Still another aspect of the invention is an immunotherapeutic method of treating an individual for a disease resulting from an allergic reaction to a bacterial infection. The method includes the steps of introducing into the individual a composition consisting essentially of a subfraction of antigens from the bacteria, including both specific and non-specific antigens, wherein the conditions of the introduction are sufficient to alleviate the symptoms of the allergic reaction. The detailed information obtained from the methods of the present invention enable treatment compositions to be rationally designed rather than designed merely by trial and error.

As an example of this aspect of the invention, a method of treating an individual for a disease associated with a microorganism as defined herein, if H. pylori induced gastritis is the disease to be treated, is to prepare a composition comprised of a polypeptide which contains one or more epitopes that are immunologically identifiable with immunogenic epitopes of H. pylori. The polypeptide is delivered to the individual to be treated in an amount sufficient to relieve an allergic reaction to H. pylori in the individual. The treatment composition is further comprised of a suitable excipient and is introduced into a patient.

Still another aspect of the present invention is a diagnostic kit including a library of microbial antigens that specifically identify a microorganism. The antigen library is packaged in a suitable container. This library includes a polypeptide containing at least one epitope which is immunologically identifiable as a microbial epitope. The antigen is affixed to a solid support. The kit also includes means for detecting immunological complexes formed between the antigens and an immunoglobulin in the biological sample. Detecting means include use of a radionuclide, radiolabel, fluorophor, chemiluminescent molecule or an enzyme, or other easily detectable labels.

Yet another aspect of the invention is a composition comprised of a structural analog of an epitope of a bacterial antigen, wherein the structural analog binds to an immunological paratope.

Another aspect of the invention is a composition comprised of a purified polyclonal antibody directed to a microbial antigen of the present invention.

Yet another aspect of the invention is a composition comprised of a monoclonal antibody directed to an antigen of a microorganism of the present invention.

The following terms are employed in this description with the follow meanings:

allergen refers to an antigen that gives rise to allergic sensitization by IgE antibodies.

allergoid refers to a chemically modified allergen that gives rise to antibody of the IgG but not IgE class, thereby reducing allergic symptoms.

allergy denotes an altered state of immune reactivity, usually denoting hypersensitivity.

antibody refers to a polypeptide or group of polypeptides which are comprised of at least one antibody combining site. An "antibody combining site", or "binding domain", is formed from the folding of variable domains of an antibody molecule(s) to form three-dimensional binding spaces with an internal surface shape and charge distribution complementary to the features of an epitope of an antigen, which allows an immunological reaction with the antigen. An antibody combining site may be formed from a heavy and/or a light chain domain (VH and VL, respectively), which form hypervariable loops which contribute to antigen binding. A "paratope" is an antibody-combining site for an epitope, the simplest form of an antigenic determinant. The term "antibody" includes, for example, vertebrate antibodies, hybrid antibodies, chimeric antibodies, altered antibodies, univalent antibodies, the Fab proteins, and single domain antibodies.

antigen is a substance capable of generating an immune response recognized by T- and/or B-cell proteins and in the present invention the term is limited to polypeptides.

biological sample refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents.

coupled refers to attachment by covalent bonds or by strong non-covalent interactions (e.g., hydrophobic interactions, hydrogen bonds, etc.). Covalent bonds may be, for example, ester, ether, phosphoester, amide, peptide, imide, carbon-sulfur bonds, carbon-phosphorus bonds, and the like.

epitope refers to an antigenic determinant of a polypeptide. An epitope could comprise 3 amino acids in a spatial conformation which is unique to the epitope. Generally an epitope consists of at least 5 such amino acids, and more usually, consists of at least 8–10 such amino acids. Methods of determining the spatial conformation of amino acids are known in the art, and include, for example, x-ray crystallography and 2-dimensional nuclear magnetic resonance.

immunogenic refers to an agent used to stimulate the immune system of a living organism, so that one or more functions of the immune system are increased and directed towards the immunogenic agent.

immunogenic polypeptide is a polypeptide that elicits a cellular and/or humoral immune response, whether alone or linked to a carrier in the presence or absence of an adjuvant.

immunologically identifiable with/as refers to the presence of epitope(s) and polypeptides(s) which are also present in the designated polypeptide(s). Immunological identity may be determined by antibody binding and/or competition in binding; these techniques are known to those of average skill in the art, and are also illustrated infra.

immunoreactive refers to a polypeptide when it is "immunologically reactive" with an antibody, i.e., when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art. An "immunoreactive" polypeptide may also be "immunogenic."

individual refers to a vertebrate, particularly members of the mammalian species, and includes, but is not limited to, domestic animals, animals used for sport, and primates, including humans.

label refers to any atom or moiety which can be used to provide a detectable (preferably quantifiable) signal, and which can be attached to a polynucleotide or polypeptide.

polypeptide refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid, including unnatural amino acids, for example, polypeptides with substituted linkages, as well as other modifications known in the art, both naturally occurring and non-naturally occurring. The term "polypeptide" does not connote the method by which the molecule was made, and thus includes naturally occurring molecules, as well as molecules made by chemical or recombinant synthesis.

support refers to any solid or semisolid surface to which a desired polypeptide. Suitable supports include glass, plastic, metal, polymer gels, and the like, and may take the form of beads, wells, dipsticks, membranes, and the like.

treatment refers to prophylaxis and/or therapy.

BRIEF DESCRIPTION OF THE DRAWINGS

FIG. 1 is a graph showing the effect of scrubbing serum with Protein A on the detection of anti-*H. pylori* IgE in a modified RAST test.

FIG. 2A is a graph showing the serum IgE levels of IgE directed to subfractions of *H. pylori* protein allergens in healthy individuals (controls).

FIG. 3 is a plot of the net total IgE immunological reactivity of serum from control and gastritis patients using all available *H. pylori* protein fractions isolated from an HPLC DEAE column; patients' values are in column 1, and control values are in column 2.

DETAILED DESCRIPTION OF THE PREFERRED EMBODIMENT

Figure 2B:
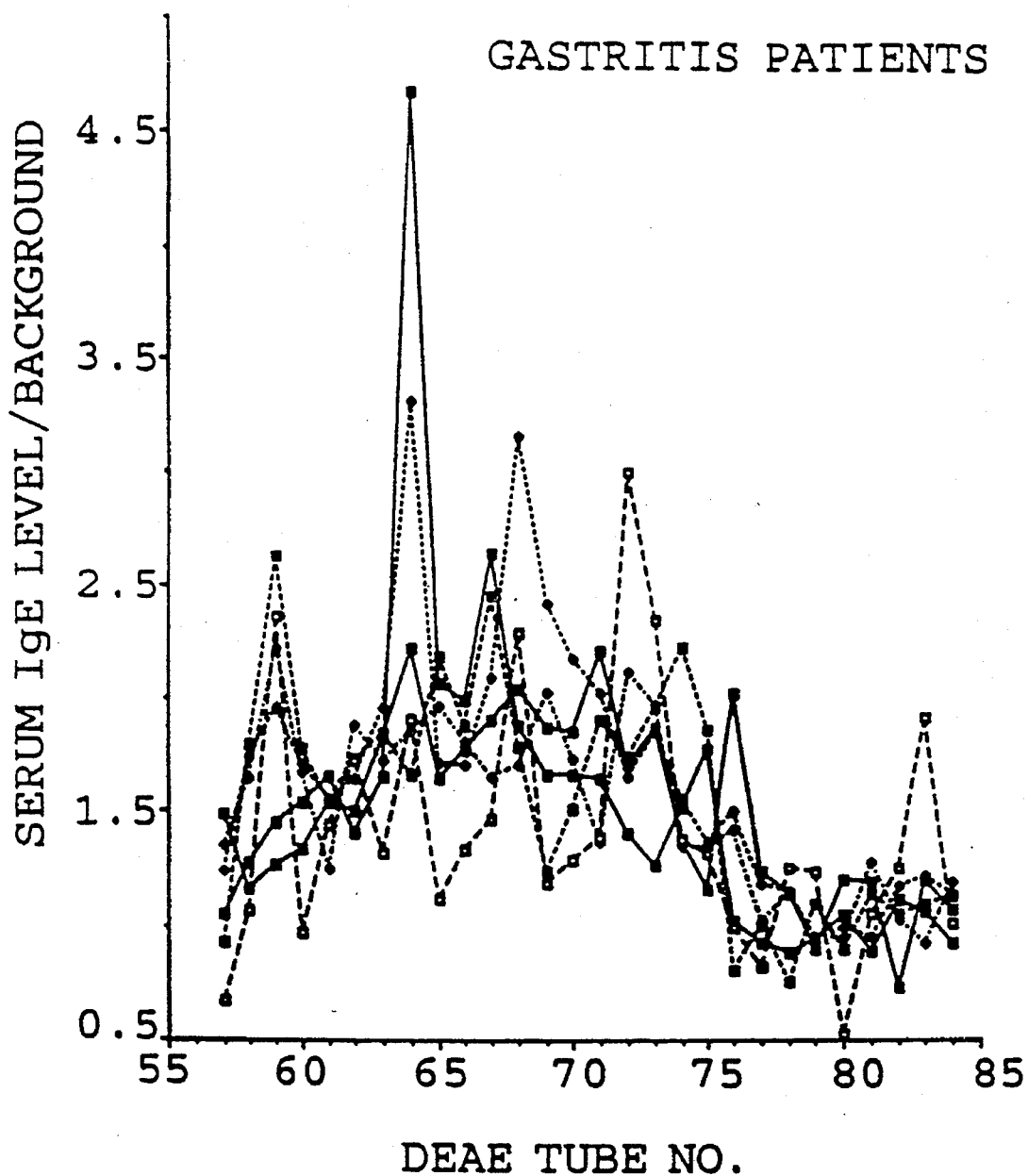
FIG. 2B is a graph showing the serum IgE levels of IgE directed to subfractions of *H. pylori* protein allergens in gastritis patients.

The present invention relates to purification of polypeptides from microorganisms to yield individual antigenic molecules. By an "individual molecule" is meant a homogeneous species as identified by molecular weight and/or isoelectric properties and solubility. In particular, the polypeptides used according to the present invention are derived from microorganisms associated with diseases and conditions for which diagnosis and treatment are needed. In the present disclosure, when the term "microorganism" is used, it is used to encompass microorganisms that are suitable for the present invention, such as bacterium, virus, mycoplasma and the like.

Proteins are extracted from preparations of a microorganism, and subfractionated in a hierarchal fashion until individual protein molecules are each in a separate subfraction, as defined by molecular weight. A preferred protocol is shown in Table 2 for the solubilization and fractionation steps. The protocol may be extended or modified in purifying antigens from a specific microorganism until individual molecules are present in the terminal subfractions and visualized on a polyacrylamide gel or other materials which separate molecules by molecular weight.

A library of antigens is selected that is specific for a particular disease or condition, by determining a set of antigens that evoke immunologic responses in percentages of individuals with the disease or condition, that are higher than in control individuals. For some embodiments, a set of antigens are selected that are unique to a microorganism in a condition as compared to a control.

The methods described here employ one or more polypeptides which contain one or more bacterial epitopes which form antigen-antibody complexes with immunoglobulins directed to bacterial antigens. To detect and quantify Ig response to bacterial allergens, for example, a Western Blot analysis or a modified RAST test as described below is suitable. For analysis of IgG, IgM or IgA response, an ELISA is suitable.

Methods of the present invention are useful for the diagnosis and treatment of bacterial related diseases. In an illustrative embodiment, percent-positive prevalence of serum IgE reactivity in peptic ulcer patients versus nasal polyp patients is shown for differential *H. pylori* antigens in Table 3. Thirty-one antigens separated into two molecular weight categories, with 50 kD as a division, are identified and listed in this Table. Eleven peptic ulcer patients and 20 nasal polyp patients were selected by direct clinical examination and, in all cases, by laboratory documentation of *H. pylori* in the ulcer patients. IgE was determined by the method of Western Blot as described herein. As illustrated in Table 3, the library of *H. pylori* antigens in this comparison, discriminates between individuals with the two diseases. It can also be seen that some antigens are present in higher percentages of ulcer patients than other antigens.

Table 4 illustrates steps leading to determining how a group of bacterial antigens are defined as a "library." A library is defined as a set of antigens that react immunologically with at least some of the affected individuals. In some embodiments, it is preferable to select all positive antigens to enhance the signal generated by immunological complexes. In other embodiments it is preferable to define as a library, a set of antigens that only reacts with a large percent of affected individuals. Although some antigens in the library may not be completely specific, in the aggregate, their effect will be minimal on test accuracy because their non-specificity will be diluted and masked, they will be diluted by the effects of the other specific antigens.

After the antigenic polypeptides are isolated and purified, they are sequenced and used to develop recombinant genetic vectors which are capable of expressing the polypeptides in a host such as *E. coli*. These methods are disclosed in a subsequent section and are useful for producing large quantities of antigens.

Table 4 lists antigens designated by identification numbers (1.12.1 and the like), by molecular weight (48 and the like), and sources (polyp 1, and the like). A "+" indicates a positive immunological response (binding with IgE), a "−" indicates no response.

The present invention further comprehends, inter alia, (i) methods to test for an immunological response of a host to a library of bacterial antigens, (ii) diagnostic kits, (iii) methods for treating diseases found to be associated with a specific immunological profile, as defined here, (iv) vaccines, (v) antibodies to the bacterial antigens detected by the methods described here and (vi) methods of producing antigens using recombinant genetic technology.

TABLE 2

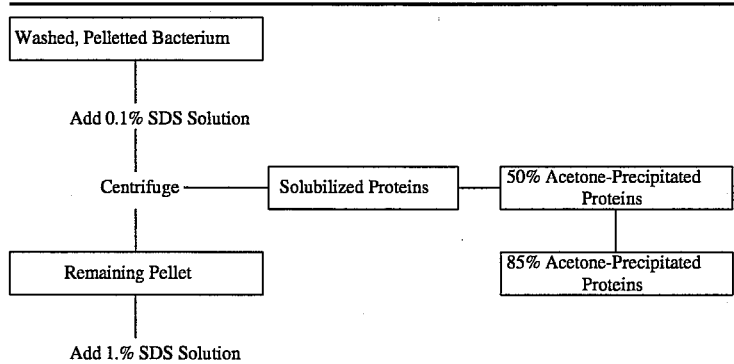

Solubilization and Fractionation of Bacterial Proteins

TABLE 2-continued

Solubilization and Fractionation of Bacterial Proteins

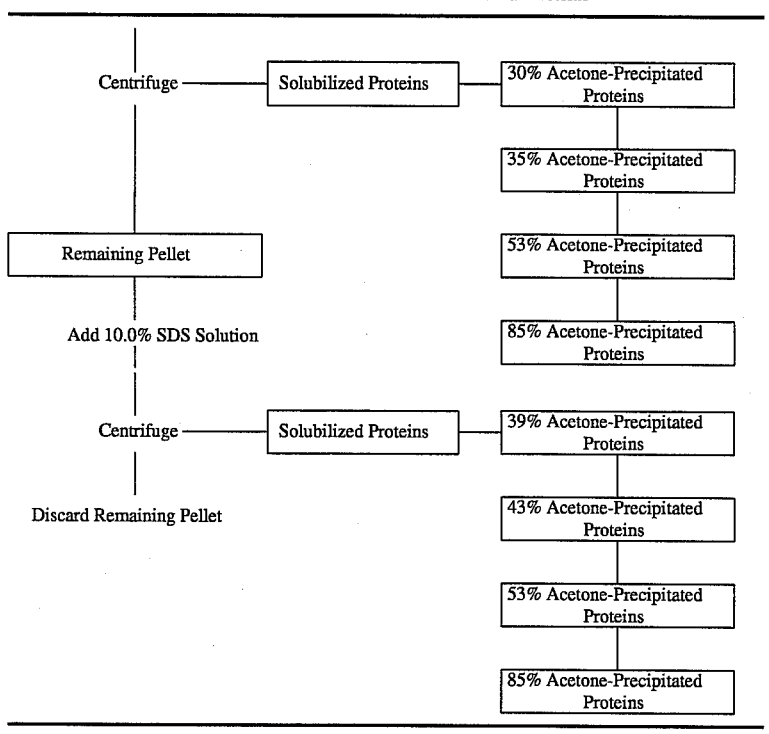

TABLE 3

Percent-Positive Prevalence of Serum IgE Reactivity of Differential H. Pylori Antigens

|  | Peptic Ulcer Patients | Nasal Polyp Patients |
|---|---|---|
| Antigens > 50 kD | | |
| 1) 2.7.1 | 55% | 5% |
| 2) 2.7.2 | 36 | 0 |
| 3) 4.7.1 | 9 | 0 |
| 5) 7.7.3 | 36 | 5 |
| Antigens < 50 kD | | |
| 6) 1.12.1 | 9 | 0 |
| 7) 1.12.2 | 9 | 0 |
| 8) 2.12.1 | 18 | 5 |
| 9) 2.12.2 | 27 | 0 |
| 10) 3.12.1 | 9 | 0 |
| 11) 3.12.2 | 45 | 5 |
| 12) 3.12.3 | 36 | 0 |
| 13) 3.12.4 | 9 | 0 |
| 14) 3.12.5 | 27 | 0 |
| 15) 3.12.6 | 36 | 0 |
| 16) 4.12.3 | 9 | 0 |
| 17) 4.12.4 | 9 | 0 |
| 18) 5.12.1 | 9 | 0 |
| 19) 5.12.2 | 27 | 5 |
| 20) 5.12.4 | 18 | 0 |
| 21) 5.12.5 | 9 | 0 |
| 22) 7.12.1 | 45 | 5 |
| 23) 7.12.4 | 9 | 0 |
| 24) 8.12.2 | 36 | 10 |
| 25) 8.12.4 | 9 | 0 |
| 26) 8.12.5 | 18 | 0 |
| 27) 9.12.1 | 18 | 0 |
| 28) 9.12.2 | 18 | 0 |
| 29) 9.12.3 | 9 | 0 |
| 30) 10.12.1 | 9 | 0 |
| 31) 10.12.4 | 9 | 0 |

TABLE 4

List of Antigens Found "Best" for Helicobocter Pylori

| Mol. Wt. | 1.12.1 / 48 | 1.12.2 / 28 | 2.7.1 / 80 | 2.7.2 / 70 | 2.7.3 / 53 | 2.12.1 / 49 | 2.12.2 / 34 | 3.12.1 / 42 | 3.12.2 / 38 | 3.12.3 / 34 | 3.12.4 / 31 | 3.12.5 / 29 | 3.12.6 / 17 | 4.7.1 / 130 | 4.12.3 / 31 |
|---|---|---|---|---|---|---|---|---|---|---|---|---|---|---|---|
| Polyp 1 | − | − | − | − | − | + | − | − | − | − | − | − | − | − | − |
| Polyp 2 | − | − | − | − | − | − | − | − | − | − | − | − | − | − | − |
| Polyp 3 | − | − | + | − | − | − | − | − | − | − | − | − | − | − | − |
| Polyp 4 | − | − | − | − | − | − | − | − | − | − | − | − | − | − | − |

TABLE 4-continued

List of Antigens Found "Best" for Helicobocter Pylori

| | | | | | | | | | | | | | | |
|---|---|---|---|---|---|---|---|---|---|---|---|---|---|---|
| Polyp 5 | − | − | − | − | − | − | − | − | − | − | − | − | − | − |
| Polyp 6 | − | − | − | − | − | − | − | − | − | − | − | − | − | − |
| Polyp 7 | − | − | − | − | − | − | − | − | − | − | − | − | − | − |
| Polyp 8 | − | − | − | − | − | − | − | − | − | − | − | − | − | − |
| Polyp 9 | − | − | − | − | − | − | − | − | − | − | − | − | − | − |
| Polyp 10 | − | − | − | − | − | − | − | − | − | − | − | − | − | − |
| Polyp 11 | − | − | − | − | − | − | − | − | − | − | − | − | − | − |
| Polyp 12 | − | − | − | − | − | − | − | − | − | − | − | − | − | − |
| Polyp 13 | − | − | − | − | − | − | − | − | − | − | − | − | − | − |
| Polyp 14 | − | − | − | − | − | − | − | − | − | − | − | − | − | − |
| Polyp 15 | − | − | − | − | − | − | − | − | − | − | − | − | − | − |
| Polyp 16 | − | − | − | − | − | − | − | − | − | − | − | − | − | − |
| Polyp 17 | − | − | − | − | − | − | − | − | − | − | − | − | − | − |
| Polyp 18 | − | − | − | − | − | − | − | − | − | − | − | − | − | − |
| Polyp 19 | − | − | − | − | − | − | − | + | − | − | − | − | − | − |
| Polyp 20 | − | − | − | − | − | − | − | − | − | − | − | − | − | − |
| PUD 1 | − | − | + | + | − | − | − | − | − | + | − | − | − | − |
| PUD 2 | − | − | − | − | − | − | + | − | − | + | − | − | − | − |
| PUD 3 | − | − | + | + | − | − | − | + | − | − | − | − | + | − |
| PUD 4 | − | − | − | − | − | − | − | − | + | − | − | + | + | − |
| PUD 5 | − | − | + | − | − | + | − | − | − | − | − | − | − | − |
| PUD 6 | + | − | + | − | − | − | − | − | − | − | − | + | + | − |
| PUD 7 | − | − | − | + | − | − | − | − | − | − | − | − | − | − |
| PUD 8 | − | − | − | − | + | − | − | − | + | − | + | − | − | + |
| PUD 9 | − | − | − | + | − | − | + | − | + | + | − | + | − | + | − |
| PUD 10 | − | + | + | − | − | − | − | − | + | − | − | − | + | − |
| PUD 11 | − | − | + | − | − | + | + | − | + | + | − | − | − | − |

| Mol. Wt. | 4.12.4 23 | 5.12.1 51 | 5.12.4 24 | 5.12.4 19 | 7.7.2 115 | 7.7.3 68 | 7.12.4 23 | 8.12.2 36 | 8.12.4 26 | 8.12.5 23 | 9.12.1 41 | 9.12.2 23 | 9.12.3 18 | 10.12.4 10 |
|---|---|---|---|---|---|---|---|---|---|---|---|---|---|---|
| Polyp 1 | − | − | − | − | − | − | − | − | − | − | − | − | − | − |
| Polyp 2 | − | − | − | − | − | − | − | − | − | − | − | − | − | − |
| Polyp 3 | − | − | − | − | − | − | − | + | − | − | − | − | − | − |
| Polyp 4 | − | − | − | − | − | − | − | − | − | − | − | − | − | − |
| Polyp 5 | − | − | − | − | − | − | − | − | − | − | − | − | − | − |
| Polyp 6 | − | − | − | − | + | − | − | − | − | − | − | − | − | − |
| Polyp 7 | − | − | − | − | − | − | − | − | − | − | − | − | − | − |
| Polyp 8 | − | − | − | − | − | − | − | − | − | − | − | − | − | − |
| Polyp 9 | − | − | − | − | − | − | − | − | − | − | − | − | − | − |
| Polyp 10 | − | − | − | − | − | − | − | − | − | − | − | − | − | − |
| Polyp 11 | − | − | − | − | − | − | − | − | − | − | − | − | − | − |
| Polyp 12 | − | − | − | − | − | − | − | − | − | − | − | − | − | − |
| Polyp 13 | − | − | − | − | − | − | − | − | − | − | − | − | − | − |
| Polyp 14 | − | − | − | − | − | − | − | − | − | − | − | − | − | − |
| Polyp 15 | − | − | − | − | − | − | − | − | − | − | − | − | − | − |
| Polyp 16 | − | − | − | − | − | − | − | + | − | − | − | − | − | − |
| Polyp 17 | − | − | − | − | − | + | − | − | − | − | − | − | − | − |
| Polyp 18 | − | − | − | − | − | − | − | − | − | − | − | − | − | − |
| Polyp 19 | − | − | − | − | − | − | − | − | − | − | − | − | − | − |
| Polyp 20 | − | − | − | − | − | − | − | − | − | − | − | − | − | − |
| PUD 1 | − | − | − | − | − | − | − | + | − | − | − | − | − | − |
| PUD 2 | − | − | − | − | + | − | − | + | − | − | − | − | − | − |
| PUD 3 | − | − | − | − | − | − | − | − | − | − | + | − | − | − |
| PUD 4 | − | − | − | + | + | − | − | − | − | + | − | − | + | + |
| PUD 5 | − | − | − | − | + | + | − | − | − | − | − | − | − | − |
| PUD 6 | − | − | − | − | − | + | − | − | − | − | − | − | − | − |
| PUD 7 | − | + | − | − | − | − | + | − | + | + | − | + | − | − |
| PUD 8 | − | − | + | − | + | + | − | − | − | − | − | − | − | − |
| PUD 9 | − | − | − | − | − | + | − | + | − | − | + | − | − | − |
| PUD 10 | − | − | − | − | − | − | − | − | − | − | − | − | − | − |
| PUD 11 | + | − | + | − | + | − | − | + | − | − | − | + | − | − |

Immunological responses may be assayed by Western Blot analysis (see Materials and Methods) or ELISA. These techniques are known to those of skill in the art (also see "MATERIALS A ND METHODS" herein). Because anti-immunoglobulin antisera are available, immunoglobulin profiles for IgE, IgA, IgM and/or IgG reactive to the same library of antigens may be examined separately. There is no need to separate the immunoglobulin isotypes present in a biological sample before testing it. The reason the effect of each isotype is detectable against a background of the other isotypes, is that there is sufficient antigen available so that binding sites are available to accommodate immunoglobulin of all types. Competition for sites does not dilute binding of an isotype such that label detection of each isotype is obscured.

Polypeptides containing one or more epitopes immunologically identifiable with epitopes of the antigens defined herein including recombinantly or synthetically produced polypeptides, and allergoids are useful in the diagnosis of diseases, and for treatment of these diseases, in accordance with the present invention.

These polypeptides also are useful for the production of antibodies, both purified polyclonal and monoclonal antibodies, directed towards microbial epitopes. The antibodies in turn are useful in the purification of polypeptides that are isolated in accordance with the present invention. In particular, monoclonal antibodies are useful for the detection of antigens containing specific epitopes and may also be useful in the production of vaccines for diseases associated with microorganisms of the present invention.

Diagnostic Kits for Diseases or Conditions Associated with a Microrganism

Polypeptides including two or more epitopes from a specific antigen library which are immunologically identifiable with epitopes of bacterial antigens are packaged in diagnostic kits. The kits are used to test a biological sample from an individual to determine if a condition is present in the individual. Diagnostic kits include the polypeptides in suitable containers and kits also include a means for detecting immunological complexes formed between the polypeptide and immunoglobulin in the biological sample, if any. Detection means include a radionuclide, radiolabel, fluorophor, chemiluminescent molecule, enzyme, or other easily detectable labels. In some cases, the polypeptides are affixed to a solid substrate such as a paper disc, or polystyrene wells. The kit also contains other suitably packaged reagents and materials needed for the particular diagnostic protocol, for example, standards, buffers, as well as instructions for conducting the test using the kit ingredients. Kits are also useful for quantifying and monitoring an immunological response. Control specimens are optionally included.

For general screening, kits preferably include as many antigens from a library as will invoke a detectable immunological response when the disease or condition is present. In other words, for screening, sensitivity should be high to detect all affected individuals, even at the expense of lower specificity. False positives can be selected out with a second level test based either on a more specific vector of antigens, perhaps a vector unique to a microorganism, by examining the pattern of responses to the individual specific antigens rather than to the aggregate response to a library, and/or quantifying the overall immunological profile reactive to a more specific set by measuring several immunoglobulin isotypes. For screening, IgE is preferred; for monitoring IgA, IgM and IgG are added to the assay.

Treatment of Disease Associated with Bacterial Allergens

In another embodiment of the invention, individuals suspected of having a propensity for, or affected with, a bacterially induced disease are treated with substances which reduce the allergic response to the microorganism. Treatment may be with, for example, a composition containing purified protein allergens. A mixture of species specific and species non-specific compositions are preferred. Treatment is with a composition containing a library of purified antigens, or with recombinant polypeptides or anti-idiotype antibodies which are immunologically identifiable with the protein allergen by virtue of one or more immunogenic epitopes which are immunologically cross-reactive with those on an *H. pylori* protein allergen. One or more allergens contained within DEAE fractions 59, 64, 66, 68, 72 and 74, the preparation of which is described in Example 1, may be particularly suitable. Even more preferable are antigens isolated and purified according to the protocol in Table 2. Embodiments of these antigens are identified in Table 4.

Treatment may also be with, for example, allergoids of protein allergens. Methods of preparing allergoids from antigens are known in the art. Typically, mild formalin or glutaraldehyde treatment of the antigen reduces the allergenicity (IgE formation) without affecting the antigenicity (IgG "blocking" antibody formation).

Treatment also can be effected, for example, with compositions containing at least one structural analog of an epitope of a protein allergen, which binds to the corresponding IgE paratope, or a mixture of naturally occurring antigens and analogs. Structural analogs are organic molecules that can assume the appropriate charge distribution and hydrophobic/hydrophilic characteristics to allow binding to the paratope in a fashion which mimics the immunologic binding of the epitope.

When the goal is alleviation of the allergic reaction by immunotherapy in the form of hyposensitization, the treated individual receives injections of a composition comprised of one or more relevant allergens continuously. Treatment is begun at a dosage low enough to avoid any local or systemic reactions, and frequent injections, usually once or twice a week are administered at increasing dosages until the highest dose the patient can tolerate without excessive local or systemic reactions is reached. This is a maintenance dose, which is then continued at less frequent intervals, usually every 1–6 weeks depending upon the individual's response. However, the actual dosage and treatment regimen depends upon the individual treated, and is determined by the person administering the treatment.

Sources of antigens suitable for the practice of the present invention include Helicobacter, Bacteroides and Streptococcus.

Vaccines

In another embodiment of the invention, the immunoreactive polypeptides (including allergens) or structural analogs of epitopes, are prepared into vaccines. Vaccines may be prepared from one or more immunogenic polypeptides. If made by recombinant technology, these polypeptides are suitably expressed in a variety of host cells (e.g., bacteria, yeast, insect, or mammalian cells). Alternatively, the antigens may be isolated from microbial preparations or prepared synthetically if the amino acid sequence is known.

The preparation of vaccines which contain, as active ingredients, an immunogenic polypeptide or structural analog having epitopes is known to one skilled in the art. Typically, such vaccines are prepared as injectable liquid solutions or suspensions. Solid forms suitable for solution in, or suspension in a liquid prior to injection are also prepared. The preparation may also be emulsified, or the protein encapsulated in liposomes.

The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP),N-acetylmuramyl-L-alanyl-D-isoglutaminylL-alanine-2-(11-21-dipalmitoyl-sn-glycero-3-hydroxyphos phoryloxy)ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an *H. pylori* immunoreactive sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate,-sodium saccharine, cellulose, magnesiumcarbonate, and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine and the like.

Vaccines within the present invention are administered in a manner compatible with the dosage formulation, and in such amount as will be prophylactically and/or therapeutically effective. The quantity to be administered, which is generally in the range of about 5 micrograms to about 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and or reenforce the immune response, for example, at 1–4 months for a second dose, and if needed, a subsequent dose(s) after several months. The dosage regimen is also, at least in part, determined by the need of the individual and be dependent upon the judgment of the practitioner.

Antibodies to Bacterial Antigens

In another embodiment of the invention, a polypeptide containing one or more epitopes immunologically identifiable with epitopes of a bacterial antigen, for example, an *H. pylori* allergen, are used to prepare antibodies to *H. pylori* epitopes, using the polypeptide as an immunizing agent, and methods known to those of skill in the art. The antibodies prepared include purified polyclonal antibodies, single-chain antibodies, monoclonal antibodies, antibody fragments, and the like. These antibodies are used, for example, for purification by affinity chromatography polypeptides of interest. More specifically, they are used to purify polypeptides containing epitopes immunologically identifiable with epitopes of *H. pylori* allergens, including the allergens themselves.

In turn, antibodies to bacterial epitopes are used for the preparation of anti-idiotype antibodies. These anti-idiotype antibodies are comprised of a region which mimics the epitope of the allergen. Anti-idiotype antibodies are synthesized using methods known in the art, and generally use antibodies directed to epitopes as an immunizing agent. In an illustrative embodiment, epitopes are from *H. pylori* as described here.

Anti-idiotype antibodies are useful in immunotherapy of individuals sensitive to allergens, as well as for the purification of and/or detection of antibodies directed to antigens containing epitopes which immunologically cross-react with the anti-idiotype antibodies.

The immunogenic polypeptides prepared as described above are used to produce polyclonal and monoclonal antibodies. If polyclonal antibodies are desired, a selected mammal (mouse, rabbit, goat, horse, etc.) is immunized with an immunogenic polypeptide bearing an epitope(s). Serum from the immunized animal is collected and treated according to known procedures. If serum containing polyclonal antibodies to the epitope contains antibodies to other antigens, the polyclonal antibody is purified by immunoaffinity chromatography. Techniques for producing and processing polyclonal antisera are known in the art. See for example, Mayer and Walker (1987). Polyclonal antibodies are isolated from an individual previously infected with the bacterial antibodies are purified by the methods discussed above.

Monoclonal antibodies directed against specific microbial epitopes are readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See U.S. Pat. Nos. 4,341,761, 4,399,121, 4,427,783, 4,444,887, 4,466,917, 4,472,500, 4,491,632 and 4,493,890. Panels of monoclonal antibodies produced against a specific set of epitopes are screened for various properties, that is, for isotype, epitope affinity and the like.

Antibodies, both monoclonal and polyclonal, which are directed against microbial epitopes are particularly useful in diagnosis, and those which are neutralizing are useful in passive immunotherapy. Monoclonal antibodies, in particular, are useful to raise anti-idiotype antibodies.

Anti-idiotype antibodies are immunoglobulins which carry an "internal image" of the antigen of the infectious agent against which protection is desired. See, for example, Nisonoff (1981), and Dreesman et al. (1985). Techniques for raising anti-idiotype antibodies are known in the art. See, for example, Grych (1985), MacNamara et al. (1984), and Uytdehaag et al. (1985). These anti-idiotype antibodies are also useful for treatment, vaccination and/or diagnosis of *H. pylori* induced gastritis and/or gastroduodenal ulcers, as well as for an elucidation of the immunogenic regions of *H. pylori* antigens.

Cloning and Expression of Antigen Proteins

Obtaining bacterial proteins as a source of purified antigens by direct extraction of proteins from a microorganism is not optimal. For many species, including *H. pylori*, it is difficult to grow adequate amounts of the microorganism in culture to provide libraries of purified antigens. A better method to obtain relatively large amounts of purified antigens is to produce them by recombinant genetic methods. However, even recombinant methods of producing antigens by cloning the genes encoding the antigens and expressing the genes in a host, will not always yield maximum quantities of protein. It therefore is preferable to clone the genes encoding these proteins and express them in a host such as *E. coli* in such a way that they can be expressed in high amounts, for example, after induction with isopropyl B-D-thiogalactopyranoside (IPTG) (Sambrook et al., 1989).

As an illustrative embodiment, the partial amino acid sequences of *H. pylori* antigen proteins that are responsible for development of specific IgE in the patients are identified. To determine an amino acid sequence, electrophoresis of the proteins on polyacrylamide gel is used to separate the proteins from minor impurities. For a specific protein, electrophoretic transfer onto PVDF (polyvinylidene fluoride, Millipore, Bedford, Mass.) membrane, identification of the protein by staining with Coomassie blue R-250, excision of the protein band, and sequencing on amino acid microsequencer, is a suitable method. If the amino-terminus of the protein is not blocked, microsequencing is suitable. If the amino terminus is blocked, the protein is subjected to cyanogen bromide cleavage which specifically cleaves the protein at the internal methionine resides. This step generates oligopeptides which are separated on a polyacrylamide gel and subjected to amino acid sequencing as described above.

On the basis of partial amino acid sequence information, oligonucleotide primers are designed which are used to clone the genes which encode specific antigen proteins. The Polymerase Chain Reaction (PCR) technique is suitable for this purpose. The isolated genes are cloned into procaryotic expression systems such as Glutathione S-transferase (GST) Gene Fusion system (Pharmacia) or Qiaxpress system (Qiagen Inc.). The GST Fusion system is designed for IPTG inducible, high-level expression of genes as a fusion protein with glutathione S-transferase at the amino-terminus. This fusion protein is purified readily from *E. coli* lysates by affinity chromatography using glutathione-sepharose. The glutathione S-transferase protein at the amino-terminus is selectively cleaved from the desired protein by site-specific protease because the expression plasmids have the specific recognition sequence for the protease at the junction. The Qiaxpress system allows the production of recombinant protein containing an amino- or carboxyterminal affinity tag consisting of six adjacent histidine residues (6XHis). The engineered 6XHis tag allows a single-step purification by nickel-chelate affinity chromatography. Some high molecular weight fusion proteins when produced in high amounts tend to aggregate causing insolubility. In such cases the former expression system has a limitation in applying affinity chromatography techniques for purification. In the Qiaexpress system, however, insoluble fusion protein is dissolved with either urea or guanidiumhydrochloride and purified on Ni-chelate affinity chromatography.

If not otherwise indicated, the practice of the present invention suitably employs conventional techniques of protein purification, microbiology, molecular biology, and immunology, which are within the skill of the art. Such techniques are explained fully in the literature.

The following examples are provided for illustrative purposes only, and not to limit the scope of the present invention. In light of the present disclosure, numerous embodiments within the scope of the claims will be apparent to those of ordinary skill in the art.

EXAMPLE 1

Isolation of *H. pylori* Protein Allergens and Covalent Coupling of the Allergens to Paper Discs A. Processing of *H. pylori*

Four grams, wet weight, of *H. pylori* (ATCC strain 43504; ATCC, Bethesda, Md., U.S.A.) were cultured essentially by the method of Smibert (1978). More specifically, *H. pylori* obtained from the American Type Culture Collection, ATCC No. 43504, was removed aseptically from its vial, suspended in 1 ml sterile Difco Brucella broth, and transferred by an in inoculating loop to 3 separate Brucella Agar plates (Anaerobe systems, San Jose, Calif.). The plates were incubated at 35° C. for 5 days in a microaerophilic atmosphere of 85% $N_2$' 10% $CO_2$, and 5% $O_2$. After incubation the plates were removed and examined. Tiny grayish-white colonies were observed. Microscopic examination of a Gram-stained smear showed large oxbowshaped and loops of Gram-negative rods (approximately 5 microns long), which are typical of *H. pylori*.

*H. pylori* in colonies from the 5 day plate were transferred to a fresh set of Brucella plates, and the plates were incubated microaerophilically at 35° C. for 3 to 5 days. After 3 days a more luxuriant growth of *H. pylori* colonies occurred. These colonies were used as the inoculum for a broth seed culture.

A broth seed culture was prepared by transferring to several 10 ml screw-capped tubes 5 ml sterile Brucella broth with 5% horse serum (GIBCO BRL), and colonies collected by swab from the plates. All tubes were incubated at 35° C. under a microaerophilic atmosphere for 3 to 5 days. If a heavy degree of turbidity was observed in the tubes after this period, the culture was examined for purity by microscopic examination of a Gram stained slide.

The broth seed culture was used as an inoculum for one liter of sterile Difco Brucella broth containing 5% horse serum. The inoculated culture was grown in a 3 liter flask by incubation at 35° C. in a microaerophilic atmosphere for 3 to 5 days. When a moderate degree of turbidity was observed, the culture was checked for purity as described above. One liter of culture generally yielded an unwashed cell amount of about 2.0 grams.

In order to isolate the protein allergens, the living organisms from the liter culture were pelleted by centrifugation at 3,000 RPM, 4° C. for 15 minutes. The attenuated bacteria was then repelleted by similar centrifugation. The pellet was resuspended in 20 ml of cold buffer containing 50 mM sodium phosphate, pH 7.3, 150 mM NaCl, 5 mM EDTA, 5 mM EGTA, 100 micrograms/ml PMSF and 100 micrograms/ml of benzamidine. Ten mL of 150–210 micron, acid-washed glass beads (Sigma, St. Louis, Mo., U.S.A.) were added, and the resulting suspension then was sonicated at setting No. 7 by means of a 400 Watt Branson Sonifer II ultrasonic cell disrupter with a regular tip. The suspension thus was sonicated for 15 minutes while being cooled in a methanol ice bath. The resulting mixture was then centrifuged as above and the supernatant saved.

B. Gradient Centrifugation

The supernatant was centrifuged for 1 hour at 100,000 g and 4° C., in a Beckman SW 40 Ti rotor (Beckman, Palo Alto, Calif., U.S.A.). To the resulting supernatant was added 0,456 cjm/ml of RbCl (Aldrich Chemical Co., Milwaukee, Wis., U.S.A.). The solution was then centrifuged at 4° C. for 48 hrs. in a Beckman 70 Ti rotor (the first 24 hours at 65,000 RPM and the second 24 hour at 48,000 RPM). The supernatant contents of each gradient tube were collected in ten equal fractions beginning at the bottom of each tube. The pellet in each tube representing most of the residual complex carbohydrates and nucleic acids containing in the pregradient supernatant was discarded.

C. Ion Exchange Chromatograph

Each gradient fraction was dialyzed against 20 mM sodium phosphate buffer, pH 7.0, at 4° C. using dialysis tubing with a 1,000 MW cutoff. An approximation the protein content per fraction was made by spectrophotometry at a wavelength of 280 nm. Ninety percent of the detected protein was found in fractions 2 through 6, inclusive; these fractions were pooled. The pooled fractions were then loaded onto a Bio-Sil DEAE analytical anion exchange HPLC column (BioRad, Richmond, Calif., U.S.A.) and a 30 minute linear gradient run achieving 100 per cent Buffer B at the end of the gradient. The equilibrating buffer (Buffer A) was 20 mm Sodium phosphate, pH 7.0. The salt containing buffer (Buffer B) was 20 mM sodiumphosphate, pH 7.0, with 1.0M NaCl. The eluted fractions were collected and the protein of each quantified as before. The flow-through (void) fraction containing macromolecules and cationic molecules was Igaded onto a Bio-Sil SP cation exchange column (BioRad) and run under the exact gradient conditions as for the DEAE run. The resulting eluted fractions were also quantified for protein.

D. Covalent Coupling of *H. pylori* Proteins to Paper Discs

CnBr activated paper discs were made essentially by the method of Ceska (1972). More specifically, paper discs (diameter 6 mm) were cut with a punch from Schleicher and Schuell 589 red ribbon filter paper. The discs were allowed to swell for 30 minutes in water. CNBR solution (5 per cent in water), was added and mixed with a mechanical stirrer for 3 minutes in a water bath at 19° C. NAOH (1M), was added dropwise to maintain the pH in the range of 10.0 to 10.5. The suspension was immediately poured into about a ten-fold excess of cold NaHCO 3 solution (5 mm, 4° C.). After thorough mixing, the solution was decanted. The wash with NAHCO 3 solution was repeated eleven times. The paper discs then were washed twice each with 500 ml of 25%, 50%, and 75% acetone in a graded series, followed by washing four times with 500 ml acetone (reagent grade, 4° C.). They were then placed on a filter paper under hood ventilation for 3 hours for drying, packaged with desiccant pouches in plastic bags, and stored at −20° C. until use.

A sufficient volume was taken from each of the elution samples collected during the ion exchange runs and diluted with 50 mM sodium carbonate buffer, pH 9.6, to yield a 3 ml solution containing 300 micrograms of protein. To each were added 30 CNBR-activated paper discs, and the mixture then was placed under gentle agitation for 48 hours at 4° C. in order to covalently couple the various proteins to their respective discs. The protein discs were washed and blocked with ethanolamine as described by Ceska, supra.

EXAMPLE 2

A Modified RAST Procedure for Detecting IgE Specific to *H. pylori* Allergens

IgE specific for *H. pylori* allergens prepared according to Example 1 was assayed for using a modified EAST procedure. Part of the procedure was essentially as described by Nalebuff et al., (1981). More specifically, an aliquot of 100 microliters of serum was incubated overnight with an appropriate allergen disc and washed three times with 50 mM phosphate buffered saline (PBS), pH 7.3, containing 0.1% Tween 20. This was followed by a second overnight incubation with $^{125}$I-labelled anti-IgE which was specific for the De-2 determinant. After being washed and prior to being counted, the allergen discs were placed into fresh tubes in a gamma counter for the amount of time previously selected by a time control. The time control consisted of 25 units of WHO-standardization IgE that was run against a PRIST antiIgE disc for the time needed for the IgE to bind 25,000 counts. This time was used in the counting of all subsequent tests.

Background levels for individual patients were determined by running each Protein A scrubbed serum (see below) against 4 blank discs, and calculating a median value representing the individual's background. Values twice this background level or greater were deemed positive. Determining the individual background level for each patient increases the precision of the assay, since it takes into account the variability corresponding directly to total serum IgE (not just that specific for the bacterial allergens).

As shown in FIG. 1, in order to detect *H. pylori* IgE, it was useful to scrub the serum samples to remove most IgG and IgA antibodies before incubation with discs containing *H. pylori* protein allergens.

Scrubbing was by incubation with recombinant Protein A/Sepharose (Zymed, S. San Francisco, Calif. U.S.A.). More specifically, two ml of serum per one ml of Protein A/Sepharose were incubated with agitation for 1 hr. The suspension was then centrifuged at 1500 RPM for 15 min. and the serum supernatants collected.

The results in FIG. 1 were obtained by taking two aliquots of the same serum from a patient with document gastritis and *H. pylori* colonization, and subjecting one of these aliquots to the scrubbing procedure. The scrubbed and unscrubbed samples from equivalent amounts of serum were then subjected to the remainder of the RAST procedure using discs containing *H. pylori* protein allergens, as described above. In the figure, the serum IgE levels detected in the scrubbed (open squares) and unscrubbed samples (closed circles) are compared. As seen from the graph, the scrubbed samples allowed the binding of IgE to the *H. pylori* protein allergens which had eluted from the DEAE column with a peak at fraction number 66. This binding was not detected in the unscrubbed sample. A repeated assay yielded similar results.

EXAMPLE 3

Analysis of Patient Sera for *H. pylori* Specific IgE

Some aspects of the present invention stem from the discovery using the present invention that individuals with chronic gastritis or gastroduodenal ulcers have serum IgE specific for protein allergens of *H. pylori*, implicating hypersensitivity to this microorganism in the etiology of the diseases.

*H. pylori* is most likely an innocuous colonizer of the gastric mucosa. It dwells just beneath the protective mucous layer and probably feeds from it without much harm to the host or to the host's protective defenses against the gastric acid. The inflammatory process recognized in chronic gastritis results in those individuals who possess the genetic proclivity toward allergy and then have the necessary MHC II antigen framework for presenting the *H. pylori* allergenic proteins as allergens. A qualitative and/or quantitative reduction in the secretion of protective mucus by the goblet cells probably occurs thus making the underlying mucosa vulnerable. In addition, a likely increase in local histamine production may take place in response to the allergic reaction. The histamine is absorbed into the vascular plexus of the stomach thus leading to an increase in gastric acid production. These two phenomena may together result in increased irritation of the early gastric lesions and, along with the constant allergic reaction to *H. pylori*, lead to lesion enlargement and chronicity.

Based upon the discovery by the inventor discussed above, immunoassays were designed to detect an *H. pylori* induced allergic reaction in individuals. In one aspect, these immunoassays utilize purified protein subfractions (allergens), and are preferable to endoscopy because they may be performed in vitro and are relatively non-invasive. In addition, the discovery allows for a novel treatment of these diseases; that is, immunotherapy with compositions comprised of at least one purified protein allergen of *H. pylori*, and/or with an allergoid of a protein allergen of *H. pylori*.

Ten consecutive gastritis/GI ulcer patients that were disease positive by endoscopy, two patients without lesions by endoscopy, and twelve apparently asymptomatic control patients were tested using the modified RAST procedure with scrubbing, as described in Example 2 and antigens prepared in accordance with Example 1.

All ten disease positive patients had measurable quantities of *H. pylori* specific IgE in their sera. The two normal endoscopy patients were IgE negative, and six of twelve asymptomatic control subjects were also IgE positive to some of the HPLC eluted proteins. As shown in FIG. 2, each IgE positive patient appeared to react to differently to the various HPLC fractionated proteins.

The prevalence of IgE positive reactivity toward the individual chromatographed fractions for each positive patient in the "asymptomatic" and "gastritis" patients was examined. There were several *H. pylori* protein fractions to which the disease group patients reacted with greater exclusivity then the "asymptomatic" patients. This more exclusive reactivity was with DEAE fractions 59, 64, 66, 68, 72 and 74.

Figure 4:
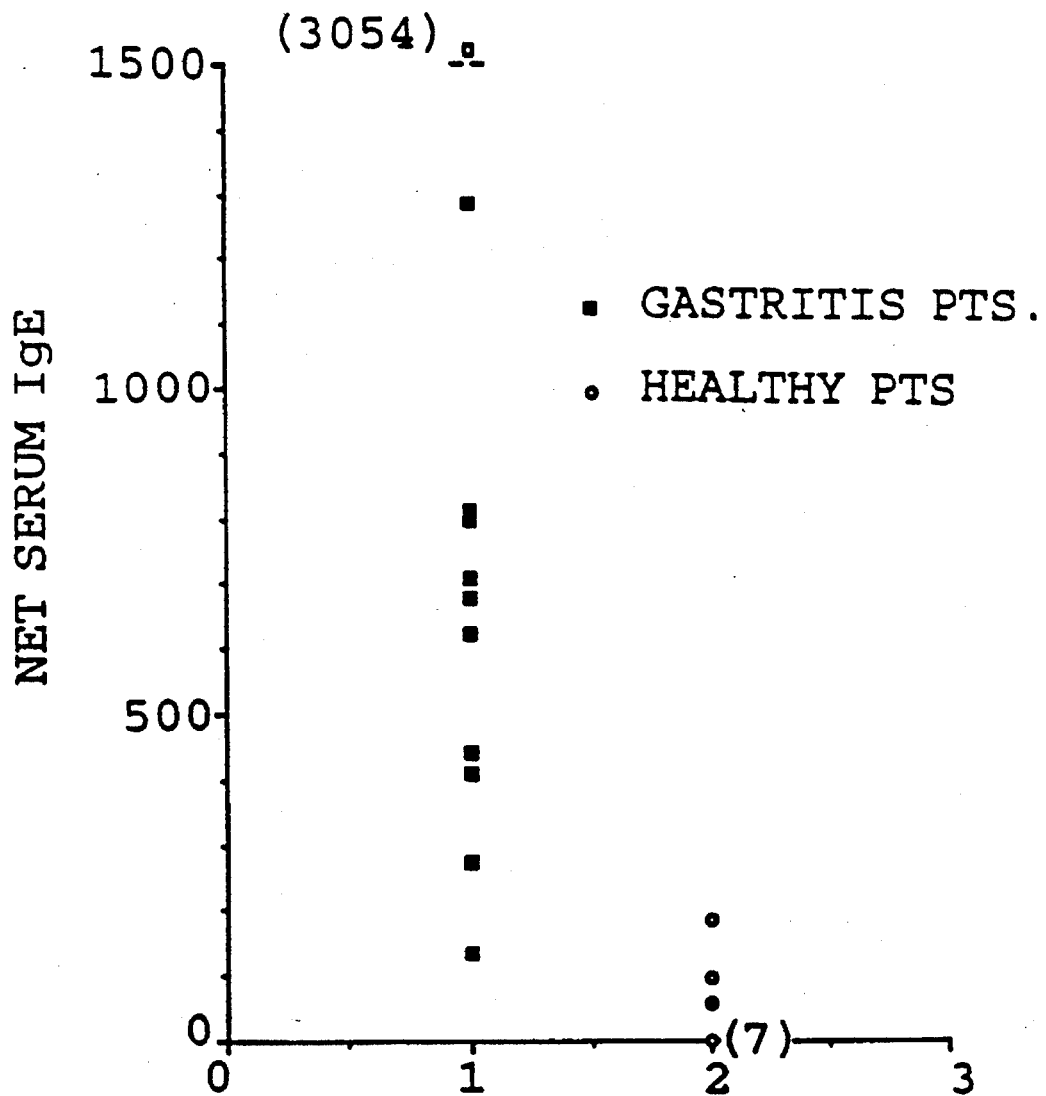
FIG. 4 is a plot of the net total IgE immunological reactivity of serum from control and gastritis patients with the proteins in fractions 59, 64, 66, 68, 72 and 74 of the HPLC DEAE column.

FIG. 3 shows a plot of the net total IgE immunological reactivity of serum from control and gastritis patients using all available *H. pylori* protein fractions isolated from an HPLC DEAE column. FIG. 4 is a plot of the net total IgE immunological reactivity of serum from control and gastritis patients with the proteins in fractions 59, 62, 65, 70, 64, 68, 71, 73, and 74.

EXAMPLE 4

Quantifying Specific IgE in Nasal Polyposis

Patients with chronic paranasal sinus disease exhibit a high positive prevalence of bacteria-specific serum IgE. Quantitation of IgE was used to discriminate among classes of patients.

A modified radioallergosorbent test method was employed wherein each serum sample was absorbed with recProtein A to remove competing non-IgE antibodies, and purified proteins extracted from 16 individual bacterial genus were used as potential allergens.

Twenty-four patients with nasal polyposis and 14 with chronic sinusiris, all refractory to conventional medical therapy and requiring endoscopic sinusotomies, were tested. Tested as controls were 10 subjects with chronic allergic rhinitis, without a history of chronic sinus disease, and possessing total serum IgE and inhalant-specific IgE levels equal to or higher than the patient group.

The results indicated that:

(1) Pretreatment of serum samples with recProtein A resulted in an increase of bacteria-specific radioallergosorbent test sensitivity.

(2) Seventeen of 24 patients with polyps, eight of 14 with chronic sinusiris, and one of 10 with chronic allergic rhinitis were determined to be IgE positive when tested with this assay.

From these results, it was concluded that:

(1) Bacteria-specific serum IgE can be quantified;

(2) Most patients with nasal polyposis and/or chronic sinusiris possess bacteria-specific IgE in their serum, while subjects with only allergic rhinitis do not; and (3) Multiple bacterial species isolated from chronically infected sinuses are capable of inducing mediated sensitization.

MATERIALS AND METHODS

Methods for Purification of Bacterial Antigens into Subfractions:

Bacterial Protein Extraction with SDS, Precipitation with Acetone

I. Extraction with 0.1, 1.0 and 10.0% SDS (Sodium Dodecyl Sulfate) Solutions

A. 0.1% SDS Extraction:
1) For each mL of PBS washed bacterial pellet add 5 mL of 0.1% SDS/20 mM Tris-HCl, pH 7.0 containing 1 mM each of EDTA(ethylenediaminetetraacetic acid), EGTA (ethyleneglycol-bis-tetraacetic acid), leupeptin, Benzamidine and PMSF (phenylmethylsulfonyl fluoride).
2) Stir contents at moderate speed for 15 min.
3) Centrifuge at 30,000 RPM for 60 min, 4° C.
4) Aliquot and freeze supernatant until needed.

B. 1.0% SDS Extraction:
1) To remaining precipitate add, for each mL of pellet, 6 mL of 1.0% SDS/20 mM Tris-HCl containing 1 mM each of EDTA, EGTA, leupeptin, benzamidine and PMSF.
2) Stir at moderate speed for 15 min. (Solution should be quite viscous.)
3) Centrifuge at 30,000 RPM for 60 min, 4° C.
4) Aliquot viscous supernatant and set aside on ice.
5) To the pellet (and slight amount of remaining viscous supernatant) add another 2 mL of 1.0% SDS extraction buffer per mL of original pellet.
6) Stir briefly.
7) Centrifuge at 30,000 RPM for 30 min, 4° C.
8) Pool viscous supernatants.
9) Slowly add 1.0M Glycine buffer, pH 2.2, to viscous supernatant while stirring until solution has lost its viscosity (should occur as solution reaches pH 2.2).

10) Centrifuge processed supernatant at 30,000 RPM for 60 min, 4° C. Discard any precipitate.
11) Aliquot supernatant and neutralize with 1.0M NaOH while stirring.
12) Centrifuge resulting suspension at 30,000 RPM for 60 min, 4° C.
13) Aliquot and freeze supernatant until needed. Discard precipitate.

C. 10.0% SDS Extraction:
1) To each mL of pellet from steps B-7 add 6 mL of 10% SDS/20 mMTris-HCl containing 1 mM each of EDTA, EGTA, leupeptin, benzamidine and PMSF.
2) Stir at moderate speed for 15 min. (Solution should be quite viscous.)
3) Centrifuge at 30,000 RPM for 60 min, 4° C.
4) Aliquot viscous supernatant and set aside on ice.
5) To the pellet (and slight amount of remaining viscous supernatant) add another 2 mL of 1.0% SDS extraction buffer per mL of original pellet.
6) Stir briefly.
7) Centrifuge at 30,000 RPM for 60 min, 4° C.
8) Pool viscous supernatants. Discard precipitate.
9) Slowly add 1.0M Glycine buffer, pH 2.2, to supernatant while stirring until solution has lost its viscosity (should occur as solution reaches pH 2.2).
10) Centrifuge processed supernatant at 30,000 RPM for 60 min, 4° C. Discard any precipitate.
11) Aliquot supernatant and neutralize with 1.0M NaOH while stirring.
12) Centrifuge resulting suspension at 30,000 RPM for 60 min, 4° C.
13) Aliquot and freeze supernatant until needed. Discard precipitate.

II. Acetone Precipitation of Proteins in 0.1, 1.0 & 10.0% SDS Extracts:

A. 0.1% SDS Extract:
1) 50% Acetone-precipitated Proteins
   a. To each mL of protein extracted from step I-A-4 slowly add (while stirring) 1.0 mL of room temperature HPLC grade acetone.
   b. Centrifuge resulting mixture at 4,000 RPM for 30 min, 4° C.
   c. Aliquot supernatant and set aside for next precipitation step.
   d. To each cc of precipitate, add 5.0 mL of 0.1% SDS in 20 mM Tris-HCL, pH 7.0.
   e. Place resulting SDS solution in boiling water bath for 5 min. (to inactivate any proteases).
   f. When cooled, dialyze solution against 1 mM Tris HCL using 3,500 MW tubing.
   g. Freeze until needed.
2) 85.0% Acetone-precipitated Proteins
   a. To each mL of supernatant from 50% precipitation step slowly add (while stirring) 4.67 mL of room temperature, HPLC grade acetone.
   b. Centrifuge resulting mixture at 4,000 RPM for 30 min, 4° C.
   c. Aliquot and discard supernatant.
   d. To each cc of precipitate, add 5.0 mL of 0.1% SDS in 20 mM Tris-HCL, pH 7.0 and gently agitate to resolubilize precipitate.
   e. Place resulting SDS solution in boiling water bath for 5 min. (to inactivate any proteases).
   f. When cooled, dialyze solution against 1 mM Tris HCL using 3,500 MW tubing.
   g. Freeze until needed.

B. 1.0% Extract
1) 30.0% Acetone-precipitated Proteins
   a. To each mL of protein extract from step I-B-11 slowly add (while stirring) 0.429 mL of room temperature, HPLC grade acetone.
   b. Centrifuge resulting mixture at 4,000 RPM for 30 min, 4° C.
   c. Aliquot supernatant and set aside for next precipitation step.
   d. To each cc of precipitate, add 5.0 mL of 0.1% SDS in 20 mM Tris-HCL, pH 7.0.
   e. Place resulting SDS solution in boiling water bath for 5 min. (to inactivate any proteases).
   f. When cooled, dialyze solution against 1 mM Tris HCL using 3,500 MW tubing.
   g. Freeze until needed.
2) 35.0% Acetone-precipitated Proteins
   a. To each mL of supernatant from 30% precipitation step slowly add (while stirring) 0.109 mL of room temperature, HPLC grade acetone.
   b. Centrifuge resulting mixture at 4,000 RPM for 30 minutes, 4° C.
   c. Aliquot and discard supernatant.
   d. To each cc of precipitate, add 5.0 mL of 0.1% SDS in 20 mM Tris-HCL, pH 7.0 and gently agitate to resolubilize precipitate.
   e. Place resulting SDS solution in boiling water bath for 5 minutes (to inactivate any proteases).
   f. When cooled, dialyze solution against 1 mM Tris HCL using 3,500 MW tubing.
   g. Freeze until needed.
3) 53.0% Acetone-precipitated Proteins
   a. To each mL of supernatant from the 35% precipitation step slowly add (while stirring) 0.59 mL of room temperature, HPLC grade acetone.
   b. Centrifuge resulting mixture at 4,000 RPM for 30 min, 4° C.
   c. Aliquot and discard supernatant.
   d. To each cc of precipitate, add 5.0 mL of 0.1% SDS in 20 mM Tris-HCL, pH 7.0 and gently agitate to resolubilize precipitate.
   e. Place resulting SDS solution in boiling water bath for 5 min. (to inactivate any proteases).
   f. When cooled, dialyze solution against 1 mM Tris HCL using 3,500 MW tubing.
   g. Freeze until needed.
4) 85.0% Acetone-precipitated Proteins
   a. To each mL supernatant from 53% precipitation step slowly add (while stirring) 4.542 mL of room temperature, HPLC grade acetone.
   b. Centrifuge resulting mixture at 4,000 RPM for 30 min, 4° C.
   c. Aliquot and discard supernatant.
   d. To each cc of precipitate, add 5.0 mL of 0.1% SDS in 20 mM Tris-HCL, pH 7.0 and gently agitate to resolubilize precipitate.
   e. Place resulting SDS solution in boiling water bath for 5 min. (to inactivate any proteases).
   f. When cooled, dialyze solution against 1 mM Tris HCL using 3,500 MW tubing.
   g. Freeze until needed.

C. 10.0% Extract:
1) 39.0% Acetone-precipitated Proteins
   a. To each mL of protein extract from step I-C-4 slowly add (while stirring) 0.64 mL of room temperature, HPLC grade acetone.

b. Centrifuge resulting mixture at 4,000 RPM for 30 minutes, 4° C.
c. Aliquot supernatant and set aside for next precipitation step.
d. To each cc of precipitate, add 5.0 mL of 0.1% SDS in 20 mM Tris-HCL, pH 7.0.
e. Place resulting SDS solution in boiling water bath for 5 minutes (to inactivate any proteases).
f. When cooled, dialyze solution against 1 mM Tris HCL using 3,500 MW tubing.
g. Freeze until needed.

2) 43.0% Acetone-precipitated Proteins
   a. To each mL supernatant from 39% precipitation step slowly add (while stirring) 0.115 mL of room temperature, HPLC grade acetone.
   b. Centrifuge resulting mixture at 4,000 RPM for 30 min, 4° C.
   c. Aliquot and discard supernatant.
   d. To each cc of precipitate, add 5.0 mL of 0.1% SDS in 20 mM Tris-HCL, pH 7.0 and gently agitate to resolubilize precipitate.
   e. Place resulting SDS solution in boiling water bath for 5 min. (to inactivate any proteases).
   f. When cooled, dialyze solution against 1 mM Tris HCL using 3,500 MW tubing.
   g. Freeze until needed.

3) 53.0% Acetone-precipitated Proteins
   a. To each mL of supernatant from the 35% precipitation step slowly add (while stirring) 0.374 mL of room temperature, HPLC grade acetone.
   b. Centrifuge resulting mixture at 4,000 RPM for 30 min, 4° C.
   c. Aliquot and discard supernatant.
   d. To each cc of precipitate, add 5.0 mL of 0.1% SDS in 20 mM Tris-HCL, pH 7.0 and gently agitate to resolubilize precipitate.
   e. Place resulting SDS solution in boiling water bath for 5 min. (to inactivate any proteases).
   f. When cooled, dialyze solution against 1 mM Tris HCL using 3,500 MW tubing.
   g. Freeze until needed.

4) 85.0% Acetone-precipitated Proteins
   a. To each mL of supernatant from 53% precipitation step slowly add (while stirring) 4.539 mL of room temperature, HPLC grade acetone.
   b. Centrifuge resulting mixture at 4,000 RPM for 30 min, 4° C.
   c. Aliquot and discard supernatant.
   d. To each cc of precipitate, add 5.0 mL of 0.1% SDS in 20 mM Tris-HCL, pH 7.0 and gently agitate to resolubilize precipitate.
   e. Place resulting SDS solution in boiling water bath for 5 min. (to inactivate any proteases).
   f. When cooled, dialyze solution against 1 mM Tris HCL using 3,500 MW tubing.
   g. Freeze until needed.

Sodium Dodecyl Sulfate Polyacrylamide Gel Electrophoresis (SDS Page)

1. Stock Solutions
   a) Acrylehmide solution (30: 0.8)

| | |
|---|---|
| Acrylamide | 30.00 g |
| Bisacrylamide | 0.80 g |

Dissolve in deionized water and make volume to 100 ml. Store in brown or aluminum foil wrapped bottle at 4° C.

b) Tris-HCL buffer, 1.0M, pH 8.8 Dissolve 12.1 g of Tris in 70 ml of deionized water, adjust pH to 8.8 with 1N HCL and make volume to 100 ml. Store at 4° C.

c) TriS-HCL buffer., 1.0M, pH 6.8 Dissolve 12.1 g of Tris in 60 ml of deionized water, adjust pH to 6.8 with 1N HCl and make volume to 100 ml. Store at 4° C.

d) 10%. sodium dodecyl sulfate (SDS) Dissolve 10 g lauryl sulfate (SDS) in 100 ml of deionized water. Store at room temp.

e) 10% Ammonium per sulfate (APS) Dissolve 500 mg of ammonium per sulfate in 5 ml of deionized water. Store frozen at −20° C.

f) Tetramethylethylenediamine (TEMED): Available commercially g) water Saturated n-butanol Add 10 ml of deionized water into 50 ml of nP butanol, had shake and let it stand till two phases are separated. Use n-butanol phase (top one).

h) 2× SDS sample buffer

| | |
|---|---|
| Tris-HCL, 1.0M, pH 6.8 | 6.24 ml |
| SDS, 10% | 10.00 ml |
| Glycerol | 10.00 ml |
| Bromophenol blue | 0.25 g |

Make up volume to 50 ml with deionized water. Store at room temp. Just before use, add 50 µl of 2-mercaptoethanol to 1.0 ml of above buffer and mix.

i) Tank Buffer (0.025M Tris 0.192M glycine, 0.1% SDS, pH 8.3)

| | |
|---|---|
| Tris | 12.1 g |
| Glycine | 57.6 g |
| SDS, 10% | 40.0 ml |

Dissolve in deionized water and made volume to 4.0 L.

j) Staining Solution

| | |
|---|---|
| (0.025% Coomassie Blue R-250, 40$ methanol, 1% acetic acid) | |
| Coomassie Blue R-250 | 2.0 g |
| Methanol | 800.0 ml |
| Stir until dissolved. | |
| Acetic Acid | 20.0 ml | k) Destaining Solution

| | |
|---|---|
| (40% methanol, 1.0% acetic acid) | |
| Methanol | 800.0 ml |
| Acetic acid | 20.0 ml |

Make volume to 2.0 with distilled water.

2. Assembling Gel Caster
   Follow instruction manual for Hoefer SE 600 Vertical Slab Gel Unit (Hoefer Scientific Instruments, San Francisco, Calif.).

3. Preparation of Separation Gel (10.0% acrylamide)

In a 50 ml flask take following:

| | |
|---|---|
| Tris-HCL, 1.0M, pH 8.8 | 9.40 ml |
| Acrylamide soln (30:0.8) | 8.30 ml |
| SDS, 10% | 0.25 ml |
| APS, 10% | 70.00 µl |
| TEMED | 40.00 µl |
| Water, deionized | 6.92 ml |

Mix and pour between the glass and the alumina plate with the help of piper. Keep top 2.5 cm empty. Layer about 200 µl of water saturated n-butanol and let the gel polymerize for at least 1 hr. Pour off n-butanol from the top of the gel and flush with deionized water. Let drain. Pour stacking gel.

4. Preparation of Stacking Gel

In a 25 ml flask take following:

| | |
|---|---|
| Tris-HCL, 1.0M, pH 6.8 | 1.6 ml |
| Acrylamide soln (30:0.8) | 2.1 ml |
| SDS, 10% | 125.0 µl |
| APS, 10% | 40.0 µl |
| TEMED | 20.0 µl |
| Deionized water | 8.6 ml |

Mix and pour. Insert 15 well comb. Make sure that there are no air bubbles below the comb teeth. Let the gel polymerize for at least 30 min. Remove the comb. Gel is ready for electrophoresis.

5. Sample Preparation

When protein sample is in solution form: add equal volume of 2× SDS sample buffer (Stock soln (h) When protein sample is in dried form: dilute 2× SDS sample buffer to 1× with deionized water and dissolve the dried protein.

Heat in the boiling water bath for 3–5 min, cool at room temp. and then load.

6. Sample Loading

Quantity of the sample to be loaded depends on the thickness of the gel and number of the wells. When 1.0 mm thick spacer and 15 well comb are used, one can load up to 80 µl of sample.

7. Running the Gel

Run the gel at constant current, 20 mA/gel till Bromophenol blue reached bottom of gel. Remove the gel and prepare to transfer contents to nitrocellulose/other blotting paper or stain.

8. Staining and Destaining

Stain the gel in Coomassie blue R-250 (solution (j) for at least 2–3 hrs. (Overnight staining usually gives better results.) Destain with solution (k) till background of the gel becomes clear. (For best results, one usually changes the destain 2–3 times.)

Western Blot Method

1. SDS-PAGE (a) Gel preparation 10.0% Acrylamide gel is made according to standard SDS-PAGE protocol. 15 well comb is used. Gels are cast at least 1.0 h before use. Separation gel can be cast on previous day; in such a case, layer water-saturated n-butanol on top of the gel. The stacking gel must be cast on the day gel is to be used.

(b) Sample preparation

Before loading individual acetone-precipitated bacterial protein fractions, determine overall protein concentration of each. Dilute individual fractions with enough SDS sample buffer to attain 25–40 µg of protein per 10 µl of sample to be loaded into each corresponding well of gel.

(c) Electrophoresis

Run at 20 mAper gel (constant current) for 4 hr or until bromophenol blue dye just runs out. Remove the gel and process for transfer onto nitrocellulose paper as follows.

2. TRANSFER OF PROTEINS ONTO NITROCELLULOSE PAPER (a) Transfer buffer preparation Dilute 10×Tris-glycine running buffer to 1× concentration, add 10% methanol while diluting. Prepare 6.0 L of transfer buffer. 10×Tris-glycine buffer recipe is given in the SDS-PAGE protocol.

(b) Getting ready for transfer

Cut 15×16 cm size nitrocellulose paper. Use gloves while handling nitrocellulose paper. Cut whitman paper #3 of 16×16.5 cm size, each gel requires six pieces. Pour 1.0 L of transfer buffer in the glass tray and soak foam sponges in the transfer buffer. Make sure that no air bubbles are left in the sponges. Two gel sponges are required for each gel.

(c) Gel Equilibration

Remove the gel after electrophoresis is run and mark the right side of gel bottom by cutting corresponding corner. Equilibrate gel in transfer buffer for 10 min. by shaking at low speed.

(d) Transfer Assembly

Following operations take place in the transfer buffer in the glass tray where sponges are soaking: Open cassette in buffer and keep black grid face up. On top of white grid, place one piece of soaked sponge, two sheets of soaked #3 Whitman paper, one sheet of soaked nitrocellulose paper, equilibrated gel (marked side should go to right bottom), two sheets of soaked #3 Whitman paper, and soaked sponge. Snap the black grid into white grid. While assembling for transfer make sure that air bubbles are not trapped between nitrocellulose paper and the gel. Transfer this assembly into the transfer chamber filled with transfer buffer. Under cooling, apply 100 volts (constant voltage) for 12.0 hrs. Then apply 1000 volts for an additional 2.0 hrs.

(e) Blocking the Protein-transferred Nitrocellulose Paper

Stir 5 g of non-fat dry milk in 100 mL of 1× PBS/0.05% Tween 20 for about 1 hr and then filter through #4 coffee filter. Add 0.05% sodium azide and stir. Remove the nitrocellulose paper from the transfer assembly and incubate with the filtered 5% non-fat dry milk, shaking at room temperature for 2.0 hrs.

3. INCUBATION WITH PRIMARY AND SECONDARY ANTIBODY (a) Primary Antibody Preparation and Incubation Dilute 200 µl of patient or control serum with 1.8 mLof 5% non-fat dry milk (NFDM) in PBS/0.4% Tween. Incubate at 4° C., shaking slowly for 20 hrs.

Remove blocking solution from protein transferred strips and add the diluted serum samples to each individual strip. Incubate with gentle agitation at room temperature for 20 hrs.

Wash the strips five times using 4 mLof PBS/0.1 Tween 20 for each strip each time. Between each washing step, incubate strip with wash buffer with gentle agitation at room temperature for 10 minutes.

After last wash, aspirate and add radio-labelled secondary antibody.

(b) Secondary Antibody Incubation

Dilute 125 I-labeled goat anti-human IgE with 5% non-fat dry milk in PBS/0.2% Tween20 so as to attain 60,000 CPM/50 µl diluent solution.

Add 2.0 ml of labeled secondary antibody solution to each strip (2.4×106 CPM/strip). Incubate under gentle agitation at room temperature for 20 hrs.

Wash strips 6 times each as described in 3-a.

Dry the strips at room temp.

Use Fuji BAS 2000 imaging system (Fuji Medical Systems, Stamford, Conn.) to analyze each strip. Determine individual qualitative and quantitative protein band IgE-reactivity A Modified RAST Test Generally, in the RAST test an allergen extract is coupled to cellulose particles or paper discs. A patient's serum containing IgE antibody or a control serum is reacted with the allergen-coupled immunosorbent. After thorough washing, labeled antibody is reacted with the immunosorbent. After further washing, the label on the separated sorbent is determined and is a measure of the amount of specific serum IgE antibodies to that allergen.

In an embodiment, the PAST test is modified to increase its sensitivity by removing IgG and/or IgA antibodies which may interfere with IgE binding to the allergen. This is particularly helpful when measuring serum IgE specific to *H. pylori* allergens that are not purified according to the SDS-acetone method of the present invention. Reactants capable of removing IgG, IgM and/or IgA are known in the art, and include, for example, Protein G, anti-human IgG and anti-human IgA, as well as Protein A. For convenience, these reactants are affixed to a solid substrate, including, for example, Sepharose. The amount of the reactants used is sufficient to remove interfering IgG and IgA, but not the IgE which is to be detected. The determination of the desired amount is by methods known to those of skill in the art.

A method of removing interfering IgG and/or IgA antibodies by incubation of the serum with Protein A is discussed in the Examples, infra. Generally, the amount of Protein A which is used is sufficient to prevent the blocking antibodies from competing with the IgE having the same specificity.

The modified RAST test also includes the use of purified protein allergens. Methods of purifying proteins are known in the art and include, for example, differential extraction, salt fractionation, chromatography on ion exchange resins, affinity chromatography and centrifugation. See, for example, Cooper (1977) and Hancock (1984). If antigens are purified by the SDS-acetone method of the present invention "scrubbing" is not needed.

CITED DOCUMENTS

The contents of the documents listed below are incorporated herein by reference, respectively, to the extent that they supplement, explain, provide a background for or teach methodology, techniques or compositions described above.

Ceska, et al. (1972) *J. Allergy and Clin. Immunol.* 49:1.
Cooper, T. G. (1977) *Tools of Biochemistry—Methods in Enzymology.* J Wiley & Sons, N.Y.
Dreesman et al. (1985) *J. Infect. Disease* 151:761.
Eaton, et al. (1989) *Infect. and Immun.* (U.S.) 57:1119
Evans, D. J. (1989) *Gastroenterology* 96:1004
Grych (1985) *Nature* 316:74.
Hancock, W. S. (1984) *CRC Handbook of HPLC for the Separation of Amino Acids, Peptides and Proteins.* CRC Press, Boca Raton, Fla.
Hupertz, et al. (1988) Eur. *J. Clin. Microbiol. Infect. Dis.* 7:576
MacNamara et al. (1984) *Science* 226:1325.
Marshall (1983) *Lancet* i:1273.
Mayer and Walker (1987) *Immunochemical Methods in Cell and Molecular Biology* (Academic Press, London).
Nalebuff, et al. (1979) *Otolaryngol. Head Neck Surg.* 87:351.
Nalebuff et al. (1981) *Otolarygol. Head Neck Surg.* 89:271.
Nisonoff, A., et al. (1981) *Clin. Immunol. Immunopathol.* 21:397.
Peterson (1991) *New England J. Med.* 374:1043.
Sambrook, J., Fritsch, E. F. Maniatis T. (1989) *Molecular Cloning: A Laboratory Manual.* 2nd ed. Vols. 1,2,3. Cold Spring Harbor Laboratory, Cold Spring Harbor, N.Y.
Slomiany et al. (1989) *Am J. Gastroenterol* 84:1273.
Smibert (1978) *Ann. Rev. Microbiol.* 32:673.
U.S. Pat. Nos. 4,341,761; 4,399,121; 4,427,783; 4,444,887; 4,466,917; 4,472,500; 4,491,632; and 4,493,890.
Uytdehaag et al. (1985) *J. Immunol.* 134:1225.

What is claimed is:

1. A method of detecting in an individual a condition associated with a microorganism, said microorganism selected from the group consisting of a bacterium, a virus, and a mycoplasma, said method comprising:

a. obtaining a library of purified and isolated antigens from a single species of microorganism wherein said library is specific for the condition;

b. measuring an antigen/antibody reaction between (i) immunoglobulin E in a biological sample from the individual, wherein immunoglobulin E is the antibody, and (ii) the isolated antigens of a library of purified antigens specific for the microorganism, and c. determining whether the condition is present, wherein the presence of said antigen/antibody reaction for said antigens indicates the presence of said condition in the individual.

2. The method of claim 1, wherein the microorganism is a bacterium.

3. The method of claim 2, wherein the condition is peptic ulcer disease and the bacterium is *Helicobacter pylori*.

4. The method of claim 2, wherein the condition is gastritis and the bacterium is *Helicobacter pylori*.

5. The method of claim 2, wherein the condition is gastric cancer and the bacterium is *Helicobacter pylori*.

6. The method of claim 2, wherein the condition is nasal polyposis and the bacterium is *Staphyloccus aureus*.

7. The method of claim 2, wherein the condition is hyperplastic sinusitis and the bacterium is *Staphylococcus aureus*.

8. The method of claim 1, wherein the antigens are isolated by a process comprising the steps of (i) solubilizing an extract of said microorganism in increasing concentrations of SDS to form fractions and (ii) subfractionating each solubilized fraction by precipitation in increasing concentrations of acetone; and (iii) selecting isolated antigens having a homogeneous molecular weight that are observed as single bands on SDS-PAGE.

9. A method of measuring in a biological sample immunoglobulin E which complexes with a bacterial antigen library, the method comprising:

(a) reacting the sample with a bacterial antigenic library coupled to a solid support, wherein said library consists of isolated and purified antigens from the same bacterial species, and wherein each antigen in the library has a homogeneous molecular weight;

(b) washing and reacting the support with labelled anti-immunoglobulin E; and (c) detecting the labeled anti-immunoglobulin E bound to the solid support.

10. A method of determining whether an individual has an immunological response to a library of bacterial antigens, said library comprising purified and isolated antigens each having a homogenous molecular weight the method comprising:

(a) providing a biological sample from an individual suspected of containing immunoglobulin E directed to antigens of the library;

(b) providing a composition consisting essentially of isolated antigens of the library;

(c) reacting the biological sample of (a) with the composition of (b) under conditions that allow immunological binding between immunoglobulin E and an antigen to which it is directed; and (d) detecting complexes formed, if any, between immunoglobulin E in the serum of (a) and a protein antigen in the composition of (b) such that the presence of the immunoglobulin is inferred and whether an individual has an immunological response is determined.

11. The method of claim 10, wherein the serum provided has been reacted with a composition capable of removing IgA and IgG from the serum in amount sufficient to remove IgG and IgA which interferes with formation of the IgE-allergen complex.

12. The method of claim 10 wherein the composition of Step b comprises protein allergens of *H. pylori*.

13. A diagnostic kit comprising a library of isolated and purified microbial antigens from the same microorganism each antigen in solution in a suitable container, and means for detecting immunological complexes formed between the library of antigens from the same microorganism and immunoglobulin E in a biological sample.

14. The kit of claim 13, wherein the library is specific for *H. pylori*.

15. The kit of claim 13, wherein the antigens are coupled to a solid support.

* * * * *

UNITED STATES PATENT AND TRADEMARK OFFICE
CERTIFICATE OF CORRECTION

PATENT NO. : 5,567,594
DATED : October 22, 1996
INVENTOR(S) : Emanuel Calenoff

Page 1 of 5

It is certified that error appears in the above-identified patent and that said Letters Patent is hereby corrected as shown below:

In the Title Page, under Other Publications,

In column 2, line 24, after "109" delete ";" and replace with --:--.

In Page 2

In column 1, line 3, under "OTHER PUBLICATIONS", replace "Idiotype" with --Idiotope--.

In column 1, line 59, italicize --Helicobacter pylori--.

In column 7, line 22, replace "PAST" with --RAST--.

In column 15, line 32, replace the second occurrence of "5.12.4" with --5.12.5--.

In column 15, line 60, replace "A ND" with --AND--.

In column 18, lines 33-34, italicize "Helicobacter, Bacteroides and Streptococcus".

In column 19, line 2, immediately after "D-isoglutaminyl" insert a hyphen -- - --.

UNITED STATES PATENT AND TRADEMARK OFFICE
CERTIFICATE OF CORRECTION

PATENT NO. : 5,567,594
DATED : October 22, 1996
INVENTOR(S) : Emanuel Calenoff It is certified that error appears in the above-identified patent and that said Letters Patent is hereby corrected as shown below:

In column 19, line 3, delete space immediately after "hydroxyphos".

In column 21, line 40, immediately after "(GST)" insert --,--.

In column 21, line 41, immediately after "system" delete carriage return and make it a continuous paragraph.

In column 21, line 54, immediately after "carboxy" insert a hyphen -- - --.

In column 23, line 5, immediately after "0" insert a period --.--.

In column 23, line 8, delete "hour" and replace with --hours--.

In column 23, line 14, delete "Chromatograph" and replace with --Chromatography--.

In column 23, line 31, delete "lgaded" and replace with --loaded--.

In column 24, line 2, replace "EAST" with --RAST--.

UNITED STATES PATENT AND TRADEMARK OFFICE
CERTIFICATE OF CORRECTION

PATENT NO. : 5,567,594
DATED : October 22, 1996
INVENTOR(S) : Emanuel Calenoff It is certified that error appears in the above-identified patent and that said Letters Patent is hereby corrected as shown below:

In column 24, line 15, replace "antioIgE" with --anti-IgE--.

In column 25, line 36, delete the second occurrence of "to".

In column 25, line 44, replace "then" with --than--.

In column 25, line 53, replace "73 ," with --73,--.

In column 26, line 2, replace "sinusiris" with --sinusitis--.

In column 26, line 13, replace "sinusiris" with --sinusitis--.

In column 26, line 19, replace "sinusiris" with --sinusitis--.

In column 26, line 22, replace "mediated" with --IgE-mediated--.

In column 27, line 11, delete the space between "m" and "M".

In column 27, line 11, immediately after "SDS/20 mM" insert a space.

In column 27, line 23, after "to" insert --viscous--.

UNITED STATES PATENT AND TRADEMARK OFFICE
CERTIFICATE OF CORRECTION

PATENT NO. : 5,567,594
DATED : October 22, 1996
INVENTOR(S) : Emanuel Calenoff It is certified that error appears in the above-identified patent and that said Letters Patent is hereby corrected as shown below:

In column 30, line 21, replace "nP butanol" with --n-butanol--.

In column 30, line 21, replace "had" with --hand--.

In column 30, line 37, replace ":" with --,--.

In column 30, line 44, replace "made" with --make--.

In column 30, line 48, replace "40S" with --40%--.

In column 30, line 61, after "2.0" insert --L--.

In column 31, line 11, replace "piper" with --pipet--.

In column 31, line 32, replace "(h)" with --(h)). --.

In column 31, line 48, replace "(j)" with --(j))--.

In column 32, line 4, replace "mAper" with --mA per--.

In column 32, line 16, replace "whitman" with --Whitman--.

In column 32, line 51, replace "mLof" with --mL of--.

In column 32, line 58, immediately after "PBS/0.1" insert --%--.

UNITED STATES PATENT AND TRADEMARK OFFICE
CERTIFICATE OF CORRECTION

PATENT NO. : 5,567,594
DATED : October 22, 1996
INVENTOR(S) : Emanuel Calenoff

It is certified that error appears in the above-identified patent and that said Letters Patent is hereby corrected as shown below:

In column 33, line 9, add a period --.-- after "reactivity".

In column 33, line 21, replace "PAST" with --RAST--.

In column 34, line 7, replace "*Otolarygol.*" with --*Otolaryngol.*--.

In the Claims

In Claim 1, line 4, replace "mycoplasma" with --mycoplasm--.

In claim 10, line 4, immediately after "weight" insert --,--.

In claim 11, line 3, after "in" insert --an--.

Signed and Sealed this

Twenty-eighth Day of July, 1998

Attest:

BRUCE LEHMAN

*Attesting Officer*        *Commissioner of Patents and Trademarks*